(12) United States Patent
DeCook et al.

(10) Patent No.: US 12,198,812 B2
(45) Date of Patent: Jan. 14, 2025

(54) SYSTEM AND METHOD FOR ANALYZING ACETABULAR CUP POSITION

(71) Applicant: DePuy Synthes Products, Inc., Raynham, MA (US)

(72) Inventors: Charles DeCook, Gainesville, GA (US); Andrew J. Cooper, Belleair Bluffs, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 165 days.

(21) Appl. No.: 17/380,137

(22) Filed: Jul. 20, 2021

(65) Prior Publication Data

US 2023/0368922 A1    Nov. 16, 2023

Related U.S. Application Data

(63) Continuation of application No. PCT/US2021/038006, filed on Jun. 18, 2021, which
(Continued)

(51) Int. Cl.
| | | |
|---|---|---|
| *G16H 50/30* | (2018.01) | |
| *G06T 7/38* | (2017.01) | |
| *G16H 30/00* | (2018.01) | |

(52) U.S. Cl.
CPC ............... *G16H 50/30* (2018.01); *G06T 7/38* (2017.01); *G16H 30/00* (2018.01);
(Continued)

(58) Field of Classification Search
CPC .......... G16H 50/30; G16H 30/00; G06T 7/38; G06T 2207/20101; G06T 2207/30008; G06T 2207/30052
See application file for complete search history.

(56) References Cited

U.S. PATENT DOCUMENTS

| | | |
|---|---|---|
| 5,715,836 A | 2/1998 | Kliegis et al. |
| 6,205,411 B1 | 3/2001 | DiGioia, III et al. |
| | (Continued) | |

FOREIGN PATENT DOCUMENTS

| | | |
|---|---|---|
| JP | 2004105551 A | 4/2004 |
| JP | 2005185767 A | 7/2005 |
| | (Continued) | |

OTHER PUBLICATIONS

Preoperative planning for implant placement with consideration of pelvic tilt in total hip arthroplasty: postoperative efficacy evaluation—2016 (Year: 2016).*
(Continued)

*Primary Examiner* — Nizar N Sivji
(74) *Attorney, Agent, or Firm* — Barnes & Thornburg LLP

(57) ABSTRACT

A system and method to identify, convey, and reduce the risk of hip dislocations following hip replacement surgery. Preoperative images are used to identify the pelvic tilt of a patient while the patient is in a sitting position, a standing position, and a supine position. Based on the pelvic tilt and pelvic mobility depicted in the preoperative images, the system can identify a quantitative and/or qualitative risk of hip dislocation when the patient is seated, standing, and lying. During surgery, an intraoperative image can confirm the acetabular cup orientation once implanted and the system can determine the risk of hip dislocation when patient is in the supine position. The system can also extrapolate the dislocation risk when the patient is seated and standing based on acetabular cup position and orientation depicted in the intraoperative image.

20 Claims, 30 Drawing Sheets

Related U.S. Application Data is a continuation of application No. 17/144,611, filed on Jan. 8, 2021, now Pat. No. 11,107,586.

(60) Provisional application No. 63/124,272, filed on Dec. 11, 2020, provisional application No. 63/069,176, filed on Aug. 24, 2020, provisional application No. 63/043,166, filed on Jun. 24, 2020.

(52) U.S. Cl.
CPC ............... *G06T 2207/20101* (2013.01); *G06T 2207/30008* (2013.01); *G06T 2207/30052* (2013.01)

(56) References Cited

U.S. PATENT DOCUMENTS

| | | | |
|---|---|---|---|
| 6,597,818 B2 | 7/2003 | Kumar et al. | |
| 9,603,711 B2 | 3/2017 | Bojarski et al. | |
| 10,182,871 B2 | 1/2019 | Wollowick et al. | |
| 10,433,914 B2 | 10/2019 | Wollowick et al. | |
| 10,610,305 B2 | 4/2020 | Wollowick et al. | |
| 10,758,198 B2 | 9/2020 | Wollowick et al. | |
| 10,765,384 B2 | 9/2020 | Wollowick et al. | |
| 10,959,782 B2 | 3/2021 | Wollowick et al. | |
| 11,107,586 B1 | 8/2021 | DeCook et al. | |
| 11,534,127 B2 | 12/2022 | Wollowick et al. | |
| 11,642,174 B2 | 5/2023 | Wollowick et al. | |
| 11,887,306 B2 | 1/2024 | Wollowick et al. | |
| 2002/0055692 A1 | 5/2002 | Tanaka et al. | |
| 2003/0176860 A1 | 9/2003 | Shimura | |
| 2004/0087852 A1 | 5/2004 | Chen et al. | |
| 2004/0171924 A1 | 9/2004 | Mire et al. | |
| 2005/0054917 A1 | 3/2005 | Kitson | |
| 2005/0203384 A1 | 9/2005 | Sati et al. | |
| 2006/0095047 A1 | 5/2006 | de la Barrera | |
| 2006/0293614 A1 | 12/2006 | Radinsky et al. | |
| 2008/0021299 A1 | 1/2008 | Meulink | |
| 2008/0056552 A1 | 3/2008 | Muller | |
| 2008/0075348 A1 | 3/2008 | Rappaport et al. | |
| 2008/0120262 A1 | 5/2008 | Habets et al. | |
| 2008/0255584 A1 | 10/2008 | Beverland et al. | |
| 2009/0089034 A1 | 4/2009 | Penney et al. | |
| 2009/0316967 A1 | 12/2009 | Dardenne et al. | |
| 2010/0030231 A1 | 2/2010 | Nitzan et al. | |
| 2010/0086181 A1 | 4/2010 | Zug et al. | |
| 2011/0093087 A1 | 4/2011 | Mcmahon et al. | |
| 2011/0313424 A1 | 12/2011 | Bono et al. | |
| 2012/0016269 A1 | 1/2012 | de la Barrera | |
| 2012/0157887 A1 | 6/2012 | Fanson et al. | |
| 2012/0194505 A1 | 8/2012 | Beck | |
| 2012/0209394 A1 | 8/2012 | Bojarski et al. | |
| 2012/0230573 A1 | 9/2012 | Ito et al. | |
| 2013/0046310 A1 | 2/2013 | Ranawat et al. | |
| 2013/0053858 A1 | 2/2013 | Penenberg | |
| 2013/0053859 A1 | 2/2013 | Penenberg | |
| 2013/0072821 A1 | 3/2013 | Odermatt et al. | |
| 2013/0304429 A1 | 11/2013 | Haimerl | |
| 2014/0093154 A1 | 4/2014 | Penenberg | |
| 2014/0378828 A1 | 12/2014 | Penenberg et al. | |
| 2015/0088145 A1 | 3/2015 | McCarthy | |
| 2015/0088146 A1 | 3/2015 | McCarthy | |
| 2015/0117608 A1 | 4/2015 | Lytle et al. | |
| 2015/0150523 A1 | 6/2015 | Sirpad et al. | |
| 2015/0227679 A1 | 8/2015 | Kamer et al. | |
| 2015/0238271 A1* | 8/2015 | Wollowick | A61B 6/505 382/128 |
| 2015/0257846 A1 | 9/2015 | Kubiak et al. | |
| 2015/0272695 A1 | 10/2015 | Kubiak et al. | |
| 2016/0100909 A1 | 4/2016 | Wollowick et al. | |
| 2016/0128654 A1 | 5/2016 | Wollowick et al. | |
| 2016/0225192 A1 | 8/2016 | Jones et al. | |
| 2017/0042619 A1 | 2/2017 | Brooks | |
| 2017/0128135 A1 | 5/2017 | McCarthy et al. | |
| 2017/0143433 A1* | 5/2017 | Fanson | G06T 7/74 |
| 2017/0202682 A1 | 7/2017 | McCarthy | |
| 2017/0224418 A1* | 8/2017 | Boettner | A61B 5/107 |
| 2017/0258526 A1* | 9/2017 | Lang | H05K 999/99 |
| 2017/0333137 A1 | 11/2017 | Wollowick et al. | |
| 2018/0161101 A1 | 6/2018 | Barsoum et al. | |
| 2018/0199995 A1* | 7/2018 | Odermatt | A61B 6/505 |
| 2018/0263699 A1 | 9/2018 | Murphy et al. | |
| 2019/0090962 A1 | 3/2019 | Boettner | |
| 2019/0298452 A1* | 10/2019 | Veilleux | G16H 30/20 |
| 2019/0350728 A1 | 11/2019 | van der Walt et al. | |
| 2019/0385303 A1* | 12/2019 | Petersen | A61B 6/12 |
| 2020/0246079 A1 | 8/2020 | Shevlev et al. | |
| 2020/0323648 A1* | 10/2020 | Samuelson | A61F 2/46 |
| 2020/0323649 A1* | 10/2020 | Schipper | G16H 30/40 |
| 2020/0405398 A1* | 12/2020 | Amanatullah | G06T 19/20 |
| 2021/0322148 A1* | 10/2021 | Mitra | A61B 34/10 |
| 2022/0202494 A1 | 6/2022 | Dressler et al. | |
| 2022/0202503 A1 | 6/2022 | Dressler et al. | |
| 2022/0249248 A1 | 8/2022 | Schipper et al. | |
| 2022/0323159 A1 | 10/2022 | Boettner et al. | |

FOREIGN PATENT DOCUMENTS

| | | |
|---|---|---|
| JP | 2007151742 A | 6/2007 |
| JP | 2009136384 A | 6/2009 |
| WO | 2007009263 A1 | 1/2007 |
| WO | 2009108683 A1 | 9/2009 |
| WO | 2013049534 A1 | 4/2013 |
| WO | 2013175471 A1 | 11/2013 |
| WO | 2014025305 A1 | 2/2014 |
| WO | 2017106858 A1 | 6/2017 |
| WO | 2018162322 A1 | 9/2018 |
| WO | 2019068194 A1 | 4/2019 |
| WO | 2019241516 A1 | 12/2019 |
| WO | 2020102886 A1 | 5/2020 |
| WO | 2020163314 A1 | 8/2020 |
| WO | 2020163316 A1 | 8/2020 |
| WO | 2020163317 A1 | 8/2020 |
| WO | 2020163318 A1 | 8/2020 |
| WO | 2020163324 A1 | 8/2020 |
| WO | 2020163328 A1 | 8/2020 |
| WO | 2020163330 A1 | 8/2020 |
| WO | 2020163352 A1 | 8/2020 |
| WO | 2020163355 A1 | 8/2020 |
| WO | 2020163358 A1 | 8/2020 |

OTHER PUBLICATIONS

Correlation of tilt of the anterior pelvic plane angle with anatomical pelvic tilt and morphological configuration of the acetabulum in patients with developmental dysplasia of the hip: a cross-sectional study—2019 (Year: 2019).*

Proposal of accurate cup placement procedure during total hip arthroplasty based on pelvic tilt discrepancies in the lateral position—2021 (Year: 2021).*

International search report for PCT/US21/38006, filed on Jun. 18, 2021 with a mailing date of Sep. 29, 2021.

Blondel et al., "Sacro-femoral-pubic angle: a coronal parameter to estimate pelvic tilt," European Spine Journal, Nov. 24, 2011, pp. 719-724, vol. 21, Springer-Verlag.

Buckland et al., "Sagittal pelvic orientation: a comparison of two methods of measurement," Bulletin of the Hospital for Joint Diseases 2017, pp. 234-240, vol. 75(4).

Lewinnek et al., "Dislocations after total hip-replacement arthroplasties," The Journal of Bone and Joint Surgery, Mar. 1978, pp. 217-220, vol. 60-A(2).

Lo Re et al., "Sacro-Femoral-Pubic Angle and Acetabular Cup Anteversion in Total Hip Arthroplasty," EC Orthopaedics, May 31, 2019, pp. 429-437, vol. 10(6).

Luthringer et al., "A Preoperative Workup of a 'Hip-Spine' Total Hip Arthroplasty Patient: A Simplified Approach to a Complex Problem," The Journal of Arthroplasty, Jan. 18, 2019, pp. S57-S70, vol. 34, Elsevier Inc.

Maratt et al., "Pelvic tilt in patients undergoing total hip arthroplasty: when does it matter?" Author Manuscript, 2014, 15 pages, Elsevier Inc.

(56) References Cited

OTHER PUBLICATIONS

Murray, "The definition and measurement of acetabular orientation," The Journal of Bone and Joint Surgery, 1993, pp. 228-232, vol. 75-B.
Pierrepont, "Patient-Specific Component Alignment in Total Hip Arthroplasty," Ph.D. Thesis, Jun. 2017, 321 pages.
Pierrepont et al., "Patient-Specific Component Alignment in Total Hip Arthroplasty," Reconstructive Review, Dec. 2016, pp. 27-33, vol. 6(4), Joint Implant Surgery & Research Foundation.
Pierrepont et al., "Variation in functional pelvic tilt in patients undergoing total hip arthroplasty," The Bone & Joint Journal, Feb. 2017, pp. 184-191, vol. 99-B.
Ragsdale et al., "Pelvic Tilt Evaluation From Frontal Radiographs: The Validity, Interobserver Reliability and Intraobserver Reproducibility of the Sacro-Femoral-Pubic Parameter," The Journal of Arthroplasty, Nov. 23, 2016, pp. 1665-1669, vol. 32, Elsevier Inc.
Zhu et al., "Quantification of Pelvic Tilt in Total Hip Arthroplasty," Clinical Orthopaedics and Related Research, Aug. 28, 2009, pp. 571-575, vol. 468(2), Springer.
Alvarez et al., "Fluoroscopic Imaging of Acetabular Cup Position During THA Through a Direct Anterior Approach," Orthopedics, Oct. 2013, pp. 776-777, vol. 36, No. 10.
Alvarez, "Fluoroscopic Imaging of Acetabular Cup Position During THA Through a Direct Anterior Approach," Orthopedics, Jan. 2014, p. 12, vol. 37, No. 1.
Babisch et al., "The Rationale for Tilt-Adjusted Acetabular Cup Navigation," The Journal of Bone & Joint Surgery, Feb. 2008, pp. 357-365, vol. 90-A, No. 2.
Bachhal et al., "A new method of measuring acetabular cup anteversion on simulated radiographs," International Orthopaedics (SICOT), May 31, 2012, pp. 1813-1818, vol. 36, Springer.
Brown et al., "Impingement in total hip replacement: mechanisms and consequences," Current Orthopaedics, 2008, pp. 376-391, vol. 22, Elsevier, Inc.
Eftekhary et al., "A systematic approach to the hip-spine relationship and its applications to total hip arthroplasty," The Bone & Joint Journal, Jul. 2019, pp. 808-816, vol. 101-B, No. 7.
Esposito et al., "Biplanar Low-Dose Radiography Is Accurate for Measuring Combined Anteversion After Total Hip Arthroplasty," HSS Journal, Feb. 5, 2019, pp. 23-29, vol. 16, No. 1, Springer Nature.
European Patent Office, Communication with Extended European Search Report for related European Patent Application No. 21828607.8, Jul. 2, 2024, 12 pages.
Hofmann et al., "Minimizing Leg-Length Inequality in Total Hip Arthroplasty: Use of Preoperative Templating and an Intraoperative X-Ray," The American Journal of Orthopedics, Jan. 2008, pp. 18-23, vol. 37(1).
Jaramaz et al., "CupAlign: Computer-Assisted Postoperative Radiographic Measurement of Acetabular Components Following Total Hip Arthroplasty," Medical Image Computing and Computer Assisted Intervention (MICCAI), 1999, pp. 876-882, Springer-Verlag.
Jointpoint, Inc., "JointPoint User Guide Version 3.4," Oct. 14, 2018, 92 pages.
Kleeman-Forsthuber et al., "Reliability of Spinopelvic Measurements That May Influence the Cup Position in Total Hip Arthroplasty," The Journal of Arthroplasty, Jun. 24, 2020, pp. 3758-3764, vol. 35, Elsevier Inc.
Labronici et al., "Positioning of the acetabular component in cemented prostheses—radiograph calculation," Revista Brasileira de Ortopedia (English Edition), 2013, pp. 62-68, vol. 48(1), Elsevier Editora Ltda.
Larose et al., "Post-Operative Measurement of Acetabular Cup Position Using X-ray/CT Registration," Medical Image Computing and Computer-Assisted Intervention (MICCAI), 2000, pp. 1104-1113, Springer-Verlag.
Liaw et al., "A New Tool for Measuring Cup Orientation in Total Hip Arthroplasties from Plain Radiographs," Clinical Orthopaedics and Related Research, Oct. 2006, pp. 134-139, vol. 451, Lippincott Wiliams & Wilkins.
Lu et al., "Reliability and Validity of Measuring Acetabular Component Orientation by Plain Anteroposterior Radiographs," Clinical Orthopaedics and Related Research, May 4, 2013, pp. 2987-2994, vol. 471, Springer.
Matta et al., "Single-Incision Anterior Approach for Total Hip Arthroplasty on an Orthopaedic Table," Clinical Orthopaedics and Related Research, Dec. 2005, pp. 115-124, vol. 441, Lippincott Williams & Wilkins.
Miki et al., "Risk of edge loading and prosthesis impingement due to posterior pelvic tilting after total hip arthroplasty," Clinical Biomechanics, 2014, pp. 607-613, vol. 29, No. 4, Elsevier, Inc.
Murphy et al., "The Safe Zone Range for Cup Anteversion Is Narrower Than for Inclination in THA," Clinical Orthopaedics and Related Research, Jan. 17, 2018, pp. 325-335, vol. 476, No. 2, Wolters Kluwer.
Myers et al., "Effect of intraoperative treatment options on hip joint stability following total hip arthroplasty," Journal of Orthopaedic Research, 2022, pp. 604-613, vol. 40, Wiley Periodicals LLC.
Penney et al., "Postoperative Calculation of Acetabular Cop Position Using 2-D-3-D Registration," IEEE Transactions on Biomedical Engineering, Jul. 2007, pp. 1342-1348, vol. 54(7), IEEE.
Vigdorchik et al., "2021 Otto Aufranc Award: A simple Hip-Spine Classification for total hip arthroplasty," The Bone & Joint Journal, Jul. 2021, pp. 17-24, vol. 103-B, No. 7.
Cuptimize, Inc., "Traditional 510(k) Application [for] Cuptimize Inc.'s Cuptimize Software," submitted confidentially to the U.S. Food and Drug Administration on Dec. 14, 2020, 215 pages (partially redacted).
Applicant, Request for Supplemental Examination of U.S. Pat. No. 11,107,586, filed Dec. 6, 2024, 81 pages.

* cited by examiner

SYSTEM AND METHOD FOR ANALYZING ACETABULAR CUP POSITION

CROSS-REFERENCE TO RELATED APPLICATIONS

This nonprovisional application is a continuation of International Application No. PCT/US21/38006 filed on Jun. 18, 2021 and claims priority to nonprovisional application Ser. No. 17/144,611, entitled "SYSTEM AND METHOD FOR ANALYZING ACETABULAR CUP POSITION," filed Jan. 8, 2021 by the same inventors, which claims priority to (1) provisional application No. 63/043,166, entitled "SYSTEM AND METHOD FOR ANALYZING ACETABULAR CUP POSITION," filed Jun. 24, 2020 by the same inventors, (2) provisional application No. 63/069,176, entitled "SYSTEM AND METHOD FOR ANALYZING ACETABULAR CUP POSITION," filed Aug. 24, 2020 by the same inventors, and (3) provisional application No. 63/124,272, entitled "SYSTEM AND METHOD FOR ANALYZING ACETABULAR CUP POSITION," filed Dec. 11, 2020 by the same inventors.

BACKGROUND OF THE INVENTION

1. Field of the Invention

This invention relates, generally, to acetabular cup implantation. More specifically, it relates to a system and method for determining and conveying the risk of hip dislocations for patients undergoing hip replacement surgery.

2. Brief Description of the Prior Art

Hip replacement surgery requires the implantation of an acetabular cup into the acetabulum in the pelvis. The acetabular cup houses the femoral head of the femoral implant in the artificial hip joint. Traditionally, surgeons performing hip replacement surgery position the acetabular cup component during surgery based upon a standard range of acceptable values for anteversion and inclination, known as the Lewinnek "Safe Zone." This safe zone is a cup inclination of 40°±10° and a cup anteversion of 15°±10°. Acetabular cups placed within the Lewinnek safe zone have traditionally been thought to be relatively safe from postoperative dislocation. Over the years, many surgeons have determined that a more ideal positioning includes the acetabular cup inserted at an inclination angle of roughly 43 degrees and an anteversion angle of roughly 23 degrees. However, there are many examples of postoperative dislocation in which the acetabular component was positioned within the Lewinnek safe zone. This postoperative data identifying dislocations within the targeted Lewinnek safe zone has led to an appreciation that hip implant stability is multifactorial and that additional data is needed to provide a more complete analysis of dislocation risk.

One of the factors understood to affect stability is the realization that a patient's effective acetabular anteversion and inclination change as they move through various positions such as sitting, standing, and supine. This is due to a change in the patient's pelvic position, known as "pelvic tilt," which occurs as a patient changes his/her position. Changes in pelvic tilt directly influence functional anteversion and inclination, which means that acetabular analysis in a single position presents an incomplete picture of data and can result in a serious dislocation risk as it does not account for potential changes due to pelvic tilt that occur in various positions.

Notably, the analysis of intraoperative inclination and anteversion data the is used to guide acetabular component placement is generally performed when the patient is positioned in a supine position—precisely the position in which dislocation risk is the lowest. The surgeon would benefit greatly from understanding how the cup position changes when a patient is in a seated or standing position, which are the functional positions that actually present a much higher dislocation risk. This would require a system to incorporate information on how pelvic tilt changes in these functional positions which would allow for the calculation of how anteversion and inclination correspondingly change. Providing data on how the acetabular position changes due to changes in pelvic tilt in different functional positions would provide surgeons with a more complete set of data to use as they assess dislocation risk.

Accordingly, what is needed is a system and method to better identify, analyze, and convey the risk of hip dislocations through a preoperative analysis of a patient's pelvis when in multiple anatomical positions. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a system and method to better identify, analyze, and convey the risk of hip dislocations through a preoperative analysis of a patient's pelvis when in multiple anatomical positions is now met by a new, useful, and nonobvious invention.

In some embodiments, the present invention includes a method for preoperatively determining inclination and anteversion for an acetabular cup component of a hip implant in several anatomical positions to determine a risk of hip dislocation in the several anatomical positions. In some embodiments, the present invention includes a computer system having one or more computers for performing the method.

The method includes acquiring a plurality of preoperative images of a patient's pelvic region. In some embodiments the plurality of preoperative images includes an anteroposterior image of the patient's pelvic region in a first anatomical position, a lateral image of the patient's pelvic region in the first anatomical position, an anteroposterior image of the patient's pelvic region when the patient is in a second anatomical position, and an image of the patient's pelvic region when the patient is in a third anatomical position. In some embodiments, the image of the patient's pelvic region when the patient is in the third anatomical position is a lateral image. Alternatively, in some embodiments the image of the patient's pelvic region when the patient is in the third anatomical position is an AP image.

In some embodiments, the first, second, and third anatomical positions are distinct from each other and each is a seated, standing, or supine position. In some embodiments, the first anatomical position is the standing position, the second anatomical position is the supine position, and the third anatomical position is the seated position.

The present invention further includes determining a sacral femoral pubic angle from the anteroposterior image of the patient's pelvic region in the first anatomical position; determining a spinal pelvic tilt angle from the lateral image of the patient's pelvic region in the first anatomical position; and determining a patient specific sacral femoral pubic constant by adding the sacral femoral pubic angle from the anteroposterior image of the patient's pelvic region in the first anatomical position to the spinal pelvic tilt angle from the lateral image of the patient's pelvic region in the first anatomical position. Determining the patient specific sacral femoral pubic constant provides a consistent relationship between an anteroposterior image and a lateral image when the patient is in the same anatomical position. As such, the present invention can use either an AP or a lateral image to precisely determine the patient's pelvic tilt in any anatomical position.

The present invention further includes determining a sacral femoral pubic angle from the anteroposterior image of the patient's pelvic region in the second anatomical position. In addition, the present invention determines a spinal pelvic tilt angle of the patient's pelvis in the second anatomical position by subtracting the sacral femoral pubic angle from the anteroposterior image of the patient's pelvic region in the second anatomical position from the patient specific sacral femoral pubic constant. Finally, the present invention determines a pelvic tilt angle from the image of the patient's pelvic region when the third anatomical position. Once the pelvic tilt data is known for each anatomical position, the calculated pelvic tilt angles in the seated position, standing position, and supine position allow a surgeon to determine how the inclination and anteversion for the acetabular cup component of the hip implant will vary in each of the seated position, standing position, and supine position.

In some embodiments, the plurality of preoperative images includes a lateral image of the patient's pelvic region when the patient is in a seated position, a lateral image of the patient's pelvic region when the patient is in a standing position, an anteroposterior image of the patient's pelvic region when the patient is in a standing position, and an anteroposterior image of the patient in a supine position.

The present invention then determines a seated spinal pelvic tilt angle either directly or indirectly through a sacral slope. Moreover, the present invention determines a patient-specific sacral femoral pubic constant from the preoperative lateral image and anteroposterior image of the patient's pelvic region when the patient is in the standing position.

Determining the sacral femoral pubic constant includes determining a standing spinal pelvic tilt angle from the lateral image either directly or indirectly through the sacral slope; determining a standing sacral femoral pubic angle from the anteroposterior image; and calculating the sacral femoral pubic constant by adding the standing sacral femoral pubic angle to the standing spinal pelvic tilt angle. Then the present invention determines a supine pelvic tilt angle of the patient from the preoperative image of the anteroposterior view of the patient in the supine position by subtracting a supine sacral femoral pubic angle from the sacral femoral pubic constant.

In some embodiments, directly determining the spinal pelvic tilt angle for any lateral image includes identifying a vertebral anatomical landmark; identifying a center point of a femoral head; establishing a vertical axis that is vertically aligned with the center point of the femoral head; and calculating the spinal pelvic tilt angle, which corresponds to an angle between the vertical axis and a line extending from the center point of the femoral head to the vertebral anatomical landmark. In some embodiments, the vertebral anatomical landmark is a midpoint on a line corresponding to a patient's sacral endplate.

In some embodiments, directly determining the spinal pelvic tilt angle for any lateral image includes digitally registering the vertebral anatomical landmark on the lateral image, digitally registering the center point of the femoral head on the lateral image, and digitally registering the vertical axis on the lateral image In some embodiments, indirectly determining the spinal pelvic tilt angle through the sacral slope for any lateral image includes identifying a vertebral anatomical landmark, establishing a horizontal axis that is horizontally aligned with a superior point on the line corresponding to the patient's sacral endplate, determining a sacral slope angle, which corresponds to an angle between the horizontal axis and the vertebral anatomical landmark, and calculating the spinal pelvic tilt angle by subtracting the sacral slope angle from a pelvic incidence of the patient. In some embodiments, the vertebral anatomical landmark is a line corresponding to the patient's sacral endplate.

In some embodiments, indirectly determining the spinal pelvic tilt angle through the sacral slope for any lateral image includes digitally registering a vertebral anatomical landmark on the lateral image and digitally registering a horizontal axis on the lateral image.

In some embodiments, determining a sacral femoral pubic angle from any anteroposterior image includes identifying a vertebral anatomical landmark; identifying the center point of the femoral head; identifying a position of a superior point on a pubic symphysis; establishing a femoral pubic line extending from the center point of the femoral head to the position of the superior point on the pubic symphysis; and calculating the sacral femoral pubic angle, which corresponds to an angle between the femoral pubic line and a line extending from the center point of the femoral head to the vertebral anatomical landmark.

In some embodiments, determining a sacral femoral pubic angle from any anteroposterior image includes digitally registering a vertebral anatomical landmark on the anteroposterior image, digitally registering the center point of the femoral head on the anteroposterior image, digitally registering a position of a superior point on a pubic symphysis on the anteroposterior image, and digitally registering a femoral pubic line extending from the center point of the femoral head to the position of the superior point on the pubic symphysis on the anteroposterior image.

Once the pelvic tilt values for each anatomical position have been determined, the present invention calculates a seated anteversion of the acetabular cup component for the seated position, a standing anteversion of the acetabular cup component for the standing position, a seated inclination of the acetabular cup component for the seated position, and a standing inclination of the acetabular cup component for the standing position.

The seated anteversion of the acetabular cup component for the seated position is based on:

$$\text{Anteversion}_{Seated} = \text{Anteversion}_{Supine} + (\text{SPT}_{Supine} - \text{SPT}_{Seated}) * \text{Ant}_{Co}$$

The $\text{Anteversion}_{Supine}$ is a predetermined supine anteversion value, $\text{SPT}_{Supine}$ is the supine pelvic tilt angle, $\text{SPT}_{Seated}$ is the seated pelvic tilt angle, and $\text{Ant}_{Co}$ is an anteversion coefficient.

The standing anteversion of the acetabular cup component for the standing position is based on:

$$\text{Anteversion}_{Standing} = \text{Anteversion}_{Supine} + (\text{SPT}_{Supine} - \text{SPT}_{Standing}) * \text{Ant}_{Co}$$

The $\text{Anteversion}_{Supine}$ is the predetermined supine anteversion value, $\text{SPT}_{Supine}$ is the supine pelvic tilt angle, $\text{SPT}_{Standing}$ is the standing pelvic tilt angle, and $\text{Ant}_{Co}$ is the anteversion coefficient.

The seated inclination of the acetabular cup component for the seated position is based on:

$$\text{Inclination}_{Seated} = \text{Inclination}_{Supine} + (\text{SPT}_{Supine} - \text{SPT}_{Seated}) * \text{Inc}_{Co}$$

The $\text{Inclination}_{Supine}$ is a predetermined supine inclination value, $\text{SPT}_{Supine}$ is the supine pelvic tilt angle, $\text{SPT}_{Standing}$ is the standing pelvic tilt angle, and $\text{Inc}_{Co}$ is an inclination coefficient.

The standing inclination of the acetabular cup component for the standing position is based on:

$$\text{Inclination}_{Standing} = \text{Inclination}_{Supine} + (\text{SPT}_{Supine} - \text{SPT}_{Standing}) * \text{Inc}_{Co}$$

The $\text{Inclination}_{Supine}$ is the predetermined supine inclination value, $\text{SPT}_{Supine}$ is the supine pelvic tilt angle, $\text{SPT}_{Standing}$ is the standing pelvic tilt angle, and $\text{Inc}_{Co}$ is the inclination coefficient.

In some embodiments, the present invention displays to a user the calculated standing inclination of the acetabular cup component, the calculated standing anteversion of the acetabular cup component, the calculated seated inclination of the acetabular cup component, and the calculated seated anteversion of the acetabular cup component. Some embodiments further include qualitatively conveying if the calculated standing inclination of the acetabular cup component, the calculated standing anteversion of the acetabular cup component, the calculated seated inclination of the acetabular cup component, and the calculated seated anteversion of the acetabular cup component are each in a low risk, medium risk, or high-risk zone for hip dislocation.

In some embodiments, the anteversion coefficient is between 0.7 and 0.8. In some embodiments, the inclination coefficient is between 0.2 and 0.4.

In some embodiments, the predetermined supine inclination value is initially set to 40. In some embodiments, the predetermined supine inclination value is adjustable by a user. In some embodiments, the predetermined supine anteversion value is initially set to 20. In some embodiments, the predetermined supine anteversion value is adjustable by a user.

Some embodiments further include retrieving an intraoperative image depicting an implanted acetabular cup component within a patient's body; determining an intraoperative inclination and an intraoperative anteversion of the implanted acetabular cup component; and calculating an intraoperative standing inclination of the acetabular cup component an intraoperative standing anteversion of the acetabular cup component, an intraoperative seated inclination of the acetabular cup component, and an intraoperative seated anteversion of the acetabular cup component. The depicted implanted acetabular cup component may be the final acetabular cup component to be permanently implanted or it may be a guide designed to mimic the final acetabular cup component.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, the term "preoperative images" referred to medical images showing the patient prior to an intended surgery. While certain embodiments may use any form of medical imaging, radiographic or x-ray imaging, alterative imaging systems may be used to capture the anatomical features of the patient. Some embodiments use 2D medical imaging. Moreover, the present invention is adapted to receive the image files in any format including, but not limited to .png, .bmp, .jpg, and DICOM format. In some embodiments, the system is configured to access one or more databases to retrieve the required images.

Intraoperative images are similar to preoperative images except that the intraoperative images are taken while the patient is in operating room ("OR") or while the surgery is ongoing. Some embodiments use 2D intraoperative medical imaging.

Figure 1:
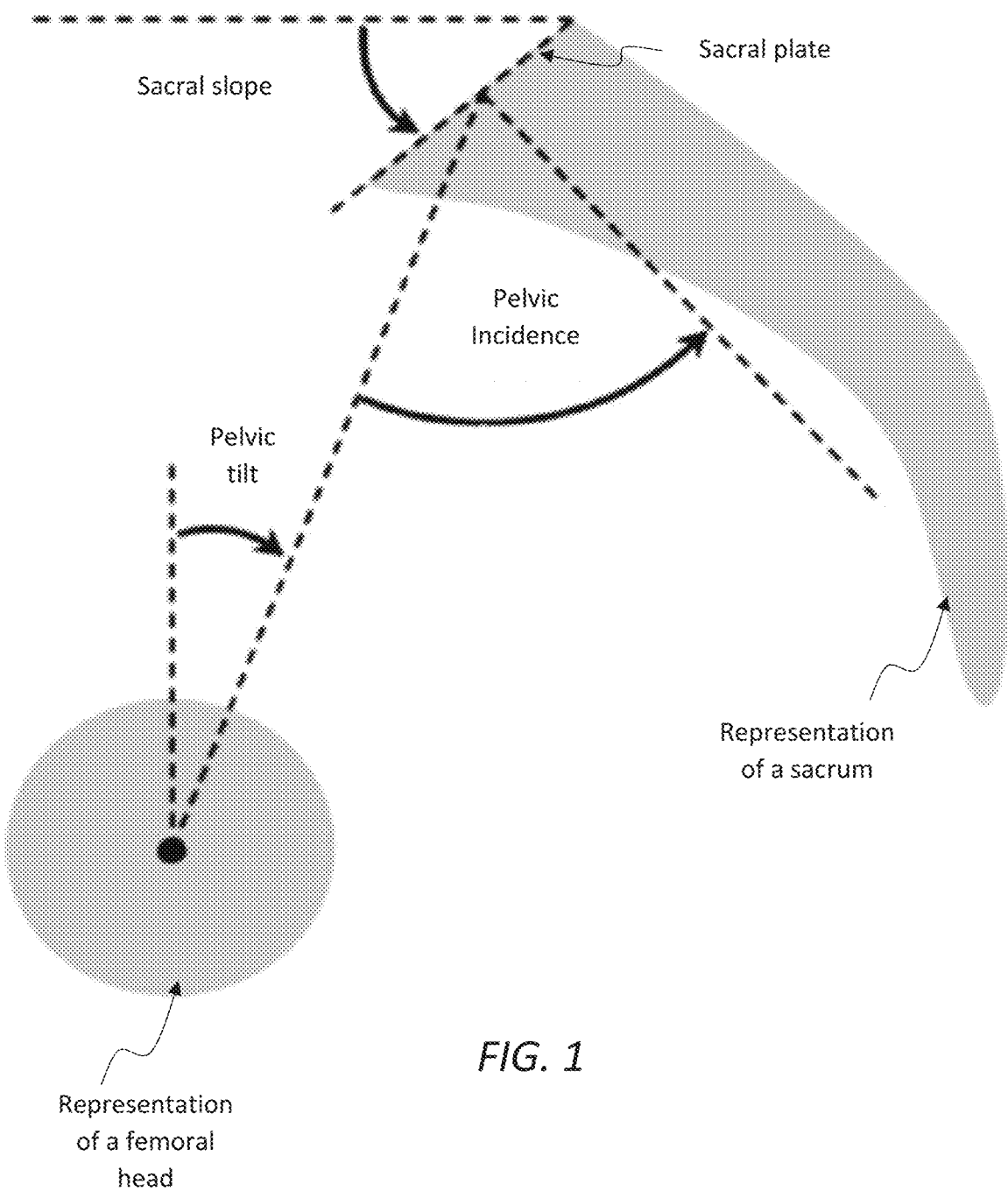
FIG. 1 is a representative diagram illustrating the relationship between the pelvic tilt, sacral slope, and pelvic incidence.

As used herein, the term "pelvic tilt" refers to the forward or backward rotation/leaning of the pelvis. An example of pelvic tilt is depicted in FIG. 1.

As used herein, "sacral slope" refers to the angle between the horizontal axis and the sacral endplate. In some embodiments, the sacral slope can be determined by relying on other vertebral anatomical landmark, however, different vertebral anatomical landmark will alter the constants and the pelvic incidence. To ensure accuracy, the same vertebral anatomical landmark should be used throughout the preoperative and intraoperative analyses.

As used herein, the "sacral-femoral-pubic angle" ("SFP angle") is calculated between a line extending from a midpoint of the vertebral anatomical landmark to the center of a femoral head, and a line extending from the superior point of the pubic symphysis to the center of a femoral head, as shown in an anteroposterior view. In some embodiments, "sacral-femoral-pubic angle" ("SFP angle") is calculated between a line extending from a midpoint of the sacral endplate to the center of a femoral head, and a line extending from the superior point of the pubic symphysis to the center of a femoral head, as shown in an anteroposterior view.

As used herein, the "spinopelvic tilt angle" ("SPT angle") is a reference of the amount of forward or backward lean of the pelvic, as shown in a lateral image. The SPT angle can be calculated as the angle between a line running from the vertebral anatomical landmark midpoint to the center of the femoral head and the vertical axis. In some embodiments, the SPT angle is calculated as the angle between a line running from the sacral endplate midpoint to the center of the femoral head and the vertical axis.

As used herein, "pelvic incidence" refers to the angle between a line perpendicular to the sacral plate at its midpoint and a line connecting this point to the femoral head axis. Pelvic incidence establishes a relationship between the pelvic tilt and the sacral slope. The tilt and the slope are inversely reciprocal. More specifically, the pelvic incidence angle equals the sum of the sacral slope angle and the SPT angle. Thus, if you know the pelvic incidence of any view (always the same) and you know either the sacral slope or SPT angle. As a result, the pelvic incidence can be used to determine the missing value of either the sacral slope or SPT angle.

As used herein, the term "supine" refers to a position in which the patient is lying in a generally flat orientation. Typically, the patient is lying on his/her back when capturing images for a hip replacement surgery.

It is also important to understand the different terminology corresponding to the various views and axes that will be discussed herein. An anteroposterior (AP) view or image is one in which an image is taken from a front side of the patient. It should be noted that an AP image could be replaced by a posteroanterior image, however, it is much more common to image a patient from an AP perspective. For ease of description and clarity, the detailed description section and exemplary figures will focus on the use of AP images.

The term "AP supine image" refers to an image taken from a front side of the patient while the patient is in a supine or lying position. While the AP image could also be a posteroanterior image, it is much more common to image a supine patient from an AP perspective. For ease of description and clarity, the embodiment of the present invention described in relation to exemplary figures will use AP supine images.

Likewise, the term "AP standing image" refers to an image taken from a front side of the patient while the patient is in a standing position. Again, the AP image could also be a posteroanterior image, however, it is much more common to image a patient from an AP perspective.

As used herein, the term "lateral image" refers to an image taken from a lateral side of the patient. A person of ordinary skill in the art will understand that a perfectly lateral view can be difficult to capture and that minor angular offsets from a perfectly lateral image are still useable with the present invention as will be explained in greater detail below.

Accordingly, the term "lateral seated image" refers to an image taken from a lateral side of the patient while the patient is in a seated position. The term "lateral relaxed seated image" refers to an image taken from a lateral side of the patient while the patient is in a relaxed seated position. Some embodiments use a preoperative lateral image when the patient is in a flexed seated position rather than a relaxed seated position. For ease of description and clarity, the embodiment of the present invention described in relation to exemplary figures only includes lateral relaxed seated images.

Finally, the term "lateral standing image" refers to an image taken from a lateral side of the patient while the patient is in a standing position.

It is also important to understand the terminology involving the orientation of the acetabular cup. When viewing a pelvis from an AP view, the inclination angle (aka the "abduction angle") of the cup is the degree of rotation about the X-axis (extends laterally across the pelvis). In other words, the inclination angle represents the inclination of the acetabular component within the coronal plane.

Figure 2:
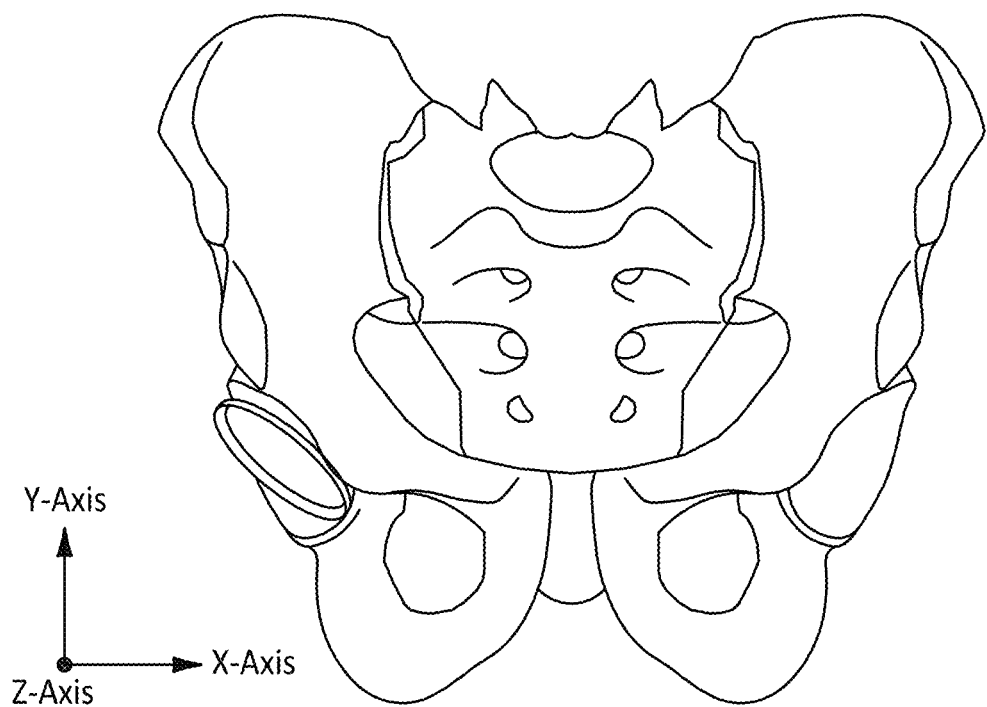
FIG. 2 is an anteroposterior view of a pelvis with the corresponding X-axis, Y-axis, and Z-axis displayed adjacent to the pelvis.

From an AP view, the anteversion angle is the degree of rotation of the cup about the Z-axis (extends perpendicular to the plane in which the pelvis resides when viewed from an AP view). In other words, anteversion is a measure of acetabular inclination within the sagittal plane. The X-, Y-, and Z-axes of a pelvis from an AP view are shown in FIG. 2.

Referring now to the specifics of the present invention, some embodiments, include a system having a memory, a user interface with a visual display, and a processor for executing a program performing at least the steps described herein. In some embodiments, the present invention is a computer executable method or is a method embodied in software for executing the steps described herein. Further explanation of the hardware and software can be found in the Hardware and software infrastructure examples section below.

The present invention includes a system and/or method to identify, convey, and reduce the risk of hip dislocations following hip replacement surgery. To do so, the present invention uses preoperative images of the patient when in at least the following anatomical positions: seated, standing, and lying (i.e., supine). The collection of preoperative images is used by a preoperative module to identify the pelvic orientation while a patient is in each of the seated, standing, and supine positions. The present invention is configured to use this information to determine an ideal range for the anteversion and inclination angle of the acetabular cup component of a hip implant to reduce the risk of dislocation in each of the anatomical positions. Some embodiments further include an intraoperative module that uses intraoperative image(s) to determine the intraoperative anteversion and inclination angle of the acetabular cup component of a hip implant to identify the risk of dislocations in each of the seated, standing, and supine positions.

Figure 3:
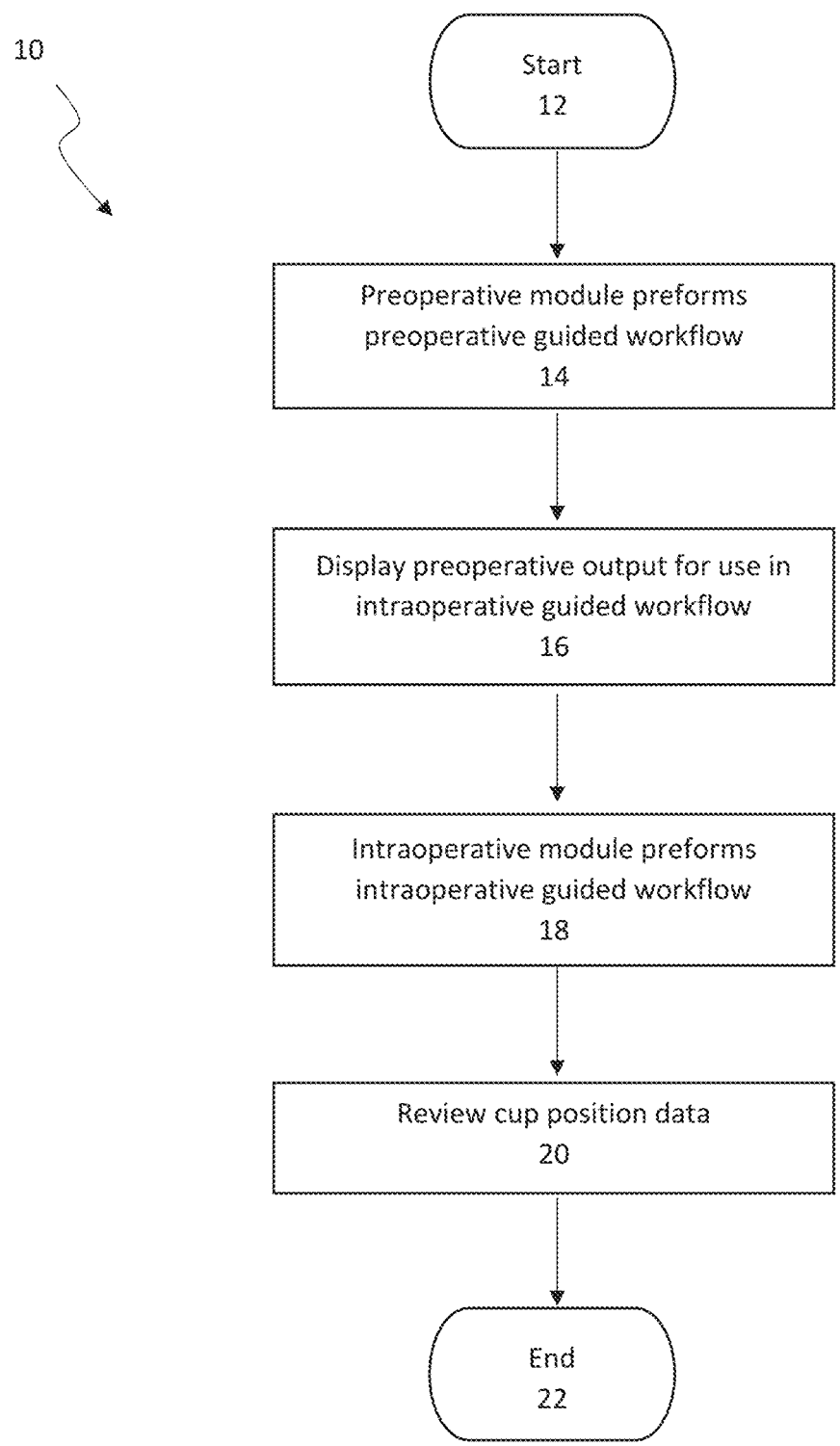
FIG. 3 is a flowchart of an embodiment of the present invention.

FIG. 3 provides a broad overview of the workflow of an embodiment of present invention generally denoted by reference numeral 10. The system or method is initiated at step 12 and a preoperative module performs a series of procedures at step 14. At step 16 the system displays the preoperative pelvic tilt data and target range for the anteversion and inclination angle of the acetabular cup component of a hip implant based on a preoperative analysis of the patient's anatomy. Some embodiments of the present invention also initiate an intraoperative module at step 18. The intraoperative module determines the anteversion and inclination angle of an implanted acetabular cup and analyzes the risk of hip dislocation in each of the seated, standing, and supine positions. The system then displays the results on a user interface at step 20. Upon satisfactory results, a user can end the program at step 22.

Figure 4:
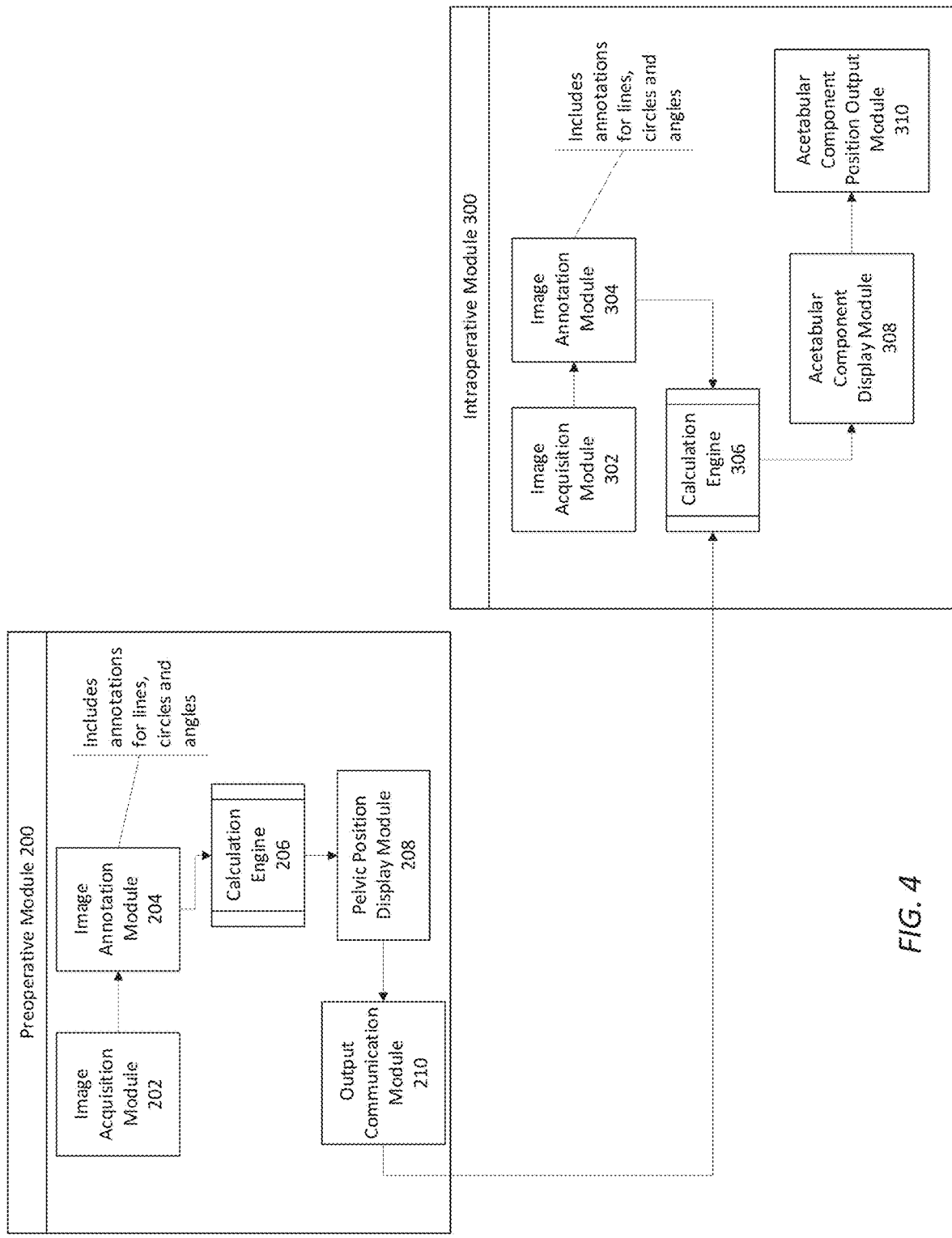
FIG. 4 is a system diagram an embodiment of the preoperative module and an embodiment of the intraoperative module.

FIG. 4 provides a general overview of the architecture of an embodiment the system of the present invention. Preoperative module 200 includes image acquisition module 202, image annotation module 204, calculation engine 206, pelvic position analysis module 208, and pelvic position output module 210. Intraoperative module 300 includes image acquisition module 302, image annotation module 304, calculation engine 306, acetabular component analysis module 308, and acetabular component position output module 310. The operational details of the various modules will be explained in greater detail below.

Preoperative Module

As will be explained in greater detail herein, the preoperative module and its corresponding workflow provide a unique ability to identify a patient specific SFP constant. The SFP constant provides the correlation between a patient's SPT angle, as shown in a lateral image, and a patient's SFP angle, as shown in an AP image. The correlation between the set of images (an AP image and a lateral image) remains constant regardless of whether the set of images capture the patient in a seated, standing, or supine position. This correlation is provided in Equation 1 below:

$$SPT_{angle} = SFP_{constant} - SFP_{angle} \qquad (Eq. 1)$$

Past research has established that the value of the SFP constant should be 75 degrees. However, an SFP constant of 75 only applies to a subset of the population and reliance on this value could ultimately have a drastic impact on the hip dislocation risk corresponding to a hip replacement surgery. Thus, some embodiments of the preoperative module are configured to determine a patient-specific SFP constant thereby allowing a surgeon to determine a patient's pelvic tilt from an AP image as needed.

Accordingly, some embodiments of the present invention include a step of analyzing (1) a preoperative AP image when the patient is in a first anatomical position and (2) a preoperative lateral image in the same anatomical position to calculate a patient specific SFP constant, which improves the precision of the analysis. This set of two images—an AP image and a lateral image—can be gathered in any anatomical position. This disclosure describes the set of images as a lateral standing image and an AP standing image because a standing position is the easiest position to clearly capture both a lateral and an AP image. However, some embodiments could use a set of lateral and AP supine images or a set of lateral and AP seated images to determine the patient specific SFP constant.

Figure 5:
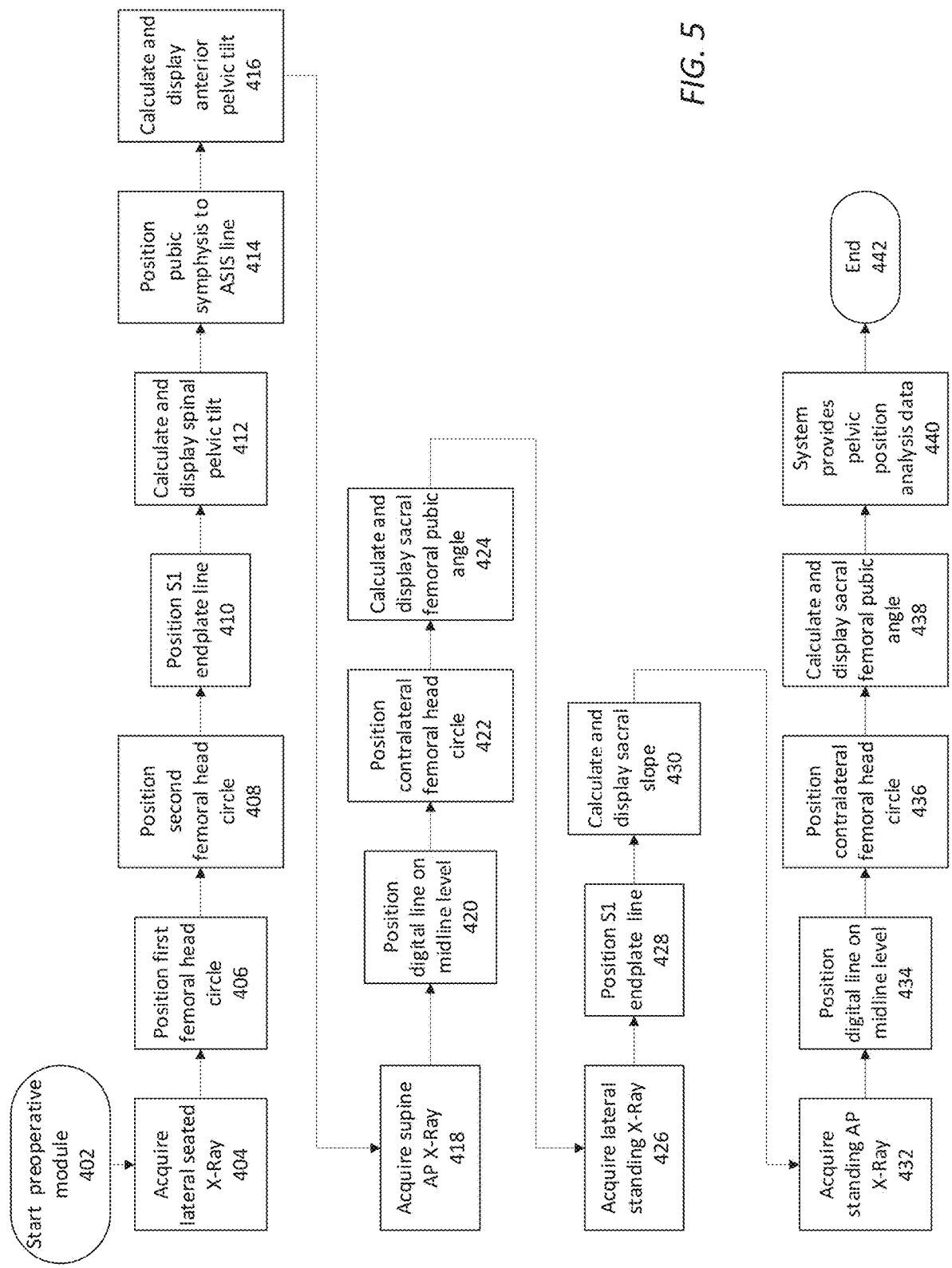
FIG. 5 is a flowchart capturing an embodiment of the steps of preoperative analysis.

Referring now to FIG. 5, an embodiment of preoperative module 200 performs the steps shown in flowchart 400. Preoperative module 200 is initiated at step 402 performs the following steps with or without user input. In some embodiments, preoperative module 200 guides the user through a predetermined workflow that begins with the receipt/acquisition of preoperative radiographic images. It should be noted that the order of image acquisition for the various anatomical positions and order of analyzing said images as shown in FIG. 5 can be rearranged without departing from the invention.

Preoperative module 200 acquires at least a seated, standing, and supine preoperative image. In some embodiments, preoperative module 200 acquires a lateral seated image, an AP supine image, a lateral standing image and/or an AP standing image. In some embodiments, the lateral seated image is a lateral relaxed seated image, which is sometimes preferable when establishing spinal tilt.

In addition, as previously noted the set of lateral and AP images may be seated or supine images rather than standing images. Similarly, the seated image may be an AP image and the supine image may be a lateral image. In some embodiments, the preoperative images of the patient in the standing, seated, and supine orientations are captured from either the AP or lateral views. In some embodiments, the preoperative images of the patient in the standing, seated, and supine orientations are captured from both the AP and lateral views. However, for the sake of brevity and clarity, this section will focus on the use of a lateral seated image, an AP supine image, a lateral standing image and an AP standing image.

In addition, some embodiments include an image orientation step to modify one or more images to better capture the patient's pelvic position/orientation as it exists in reality. Alternatively, the image capturing device is first properly oriented prior to capturing the image to ensure that the image depicts the pelvis in the same position/orientation as it exists in reality. In some embodiments, the user is provided with the option to manually rotate the preoperative image as needed to better capture the true orientation of a patient's pelvis in reality.

As previously explained, the preoperative images are used to identify the pelvic tilt and how the pelvic tilt changes in each of the seated, standing, and lying positions, which is used to determine an ideal range for the anteversion and inclination angle of the acetabular cup component of a hip implant. Thus, preoperative module 200 is configured to determine the pelvic tilt in the various anatomical positions from the preoperative images.

In some embodiments, the pelvic tilt is determined directly by measuring the spinal pelvic tilt (SPT) angle from a lateral view. In some embodiments, the pelvic tilt is measured indirectly through the angle of the sacral slope from a lateral view by relying on the pelvic incidence. Some embodiments determine the pelvic tilt indirectly by measuring sacral femoral pubic (SFP) angle as seen in an AP view. The different approaches will be discussed in connection with certain images and certain anatomical positions; however, it should be noted that the pelvic tilt for any of the anatomical positions (seated, standing, and supine) can be determined from either (1) lateral images using the SPT angle and/or the sacral slope or (2) AP images using the SFP angle.

Regardless of how the pelvic tilt angle is determined, the present invention uses anatomical landmarks to determine the relevant angles and pelvic tilt. The anatomical landmark may be points, lines, circles, or other types of digitally registerable annotations corresponding to one or more aspects of the patient's anatomy. In some embodiments, the anatomical landmarks are determined manually by a user whereas some embodiments image annotation module 204 automatically identifies the anatomical landmarks through image recognition software or machine learning algorithms. Some embodiments employ a mix of automated and manual identification of the anatomical landmarks. Moreover, some embodiments, allow the user to modify the location of the visually displayed anatomical landmarks points to account for imaging or location errors.

In some embodiments, some or all of the anatomical landmarks are digitally inserted or overlaid onto the images to provide a visual indication of the location of the anatomical landmarks. While different methods of visually displaying the landmarks may be used, the term "digitally register" will be used herein to refer to any method used to visually depict an anatomical landmark on a digital image. In some embodiments, preoperative module 200 visually displays to a user each instance in which an anatomical landmark is digitally registered on one of the preoperative images similar to FIGS. 6-19.

Some embodiments may perform the steps of determining the SPT angle, sacral slope, and/or SFP angle without visually displaying the anatomical landmarks or other visual indicia. Some embodiments may visually display only a subset of the anatomical landmarks or other visual indicia. However, the detailed description section and the exemplary images will focus on embodiments in which each step is visually displayed to better convey the steps of the present invention.

Determining Pelvic Tilt in the Various Anatomical Positions

Referring now to FIGS. 4 and 5 in combination, an embodiment of preoperative module 200 includes image acquisition module 202 acquiring a plurality of preoperative images at steps 404, 418, 426, and 432. As previously noted, the order of image acquisition for the various anatomical positions and order of analyzing said images as shown in FIG. 5 can be rearranged without departing from the invention. For example, some embodiments perform steps 426-440 in order to determine a patient specific SFP constant prior to determining the pelvic tilt from an AP image such as in step 424.

In addition, the method of determining the pelvic tilt in each anatomical position can vary depending on whether the image is an AP image or lateral image. Moreover, the method for determining the pelvic tilt from a lateral image can vary depending on the ease of which certain anatomical features can be identified. These various methods will be described in more detail below in relation to the exemplary flowcharts of FIGS. 4 and 5 and the exemplary images of FIGS. 6-19. For the sake of brevity and clarity determining pelvic tilt in a lateral image by relying on the femoral head(s) is described in relation to an acquired lateral seated preoperative image in steps 406-412 in FIG. 5; determining pelvic tilt in a lateral image by relying on the sacral slope is described in relation to an acquired lateral standing preoperative image in steps 428-430 in FIG. 5; and determining the pelvic tilt from an AP image is described in steps 420-424 of FIG. 5 in relation to the preoperative supine AP image. However, the method of determining the pelvic tilt in each anatomical position can vary depending on whether the image is an AP image or lateral image.

Seated Pelvic Tilt

Referring back to FIGS. 4 and 5 in combination, an embodiment of preoperative module 200 includes image acquisition module 202 acquiring a lateral seated preoperative image at step 404. Image annotation module 204 then performs steps 406 through 410, which are exemplified in FIGS. 6-9, in order to directly determine the SPT angle. As previously noted, some embodiments alternatively calculate the sacral slope in the seated lateral image and some embodiments calculate the SPT angle through the SFP angle shown in a seated AP image.

Figure 6:
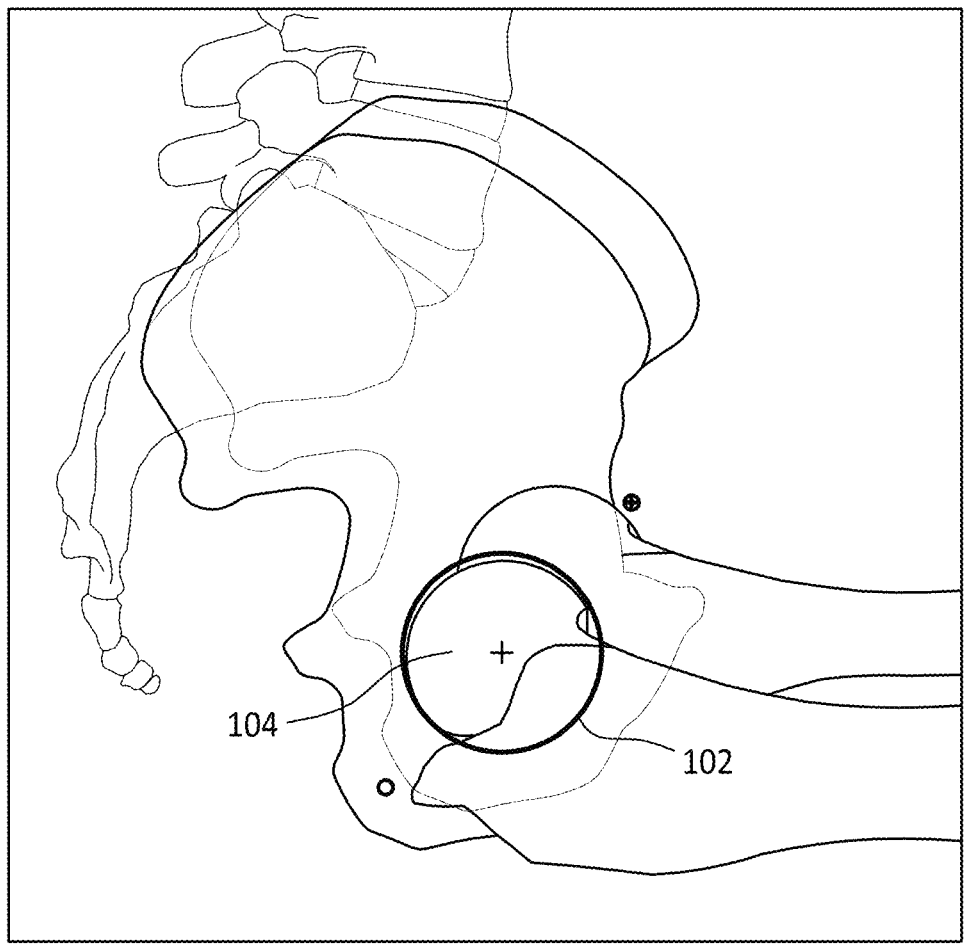
FIG. 6 is an exemplary preoperative lateral image of a patient's pelvic region when the patient is in a seated position. The figure depicts the step in which a circle is drawn around one of the femoral heads.
Figure 7:
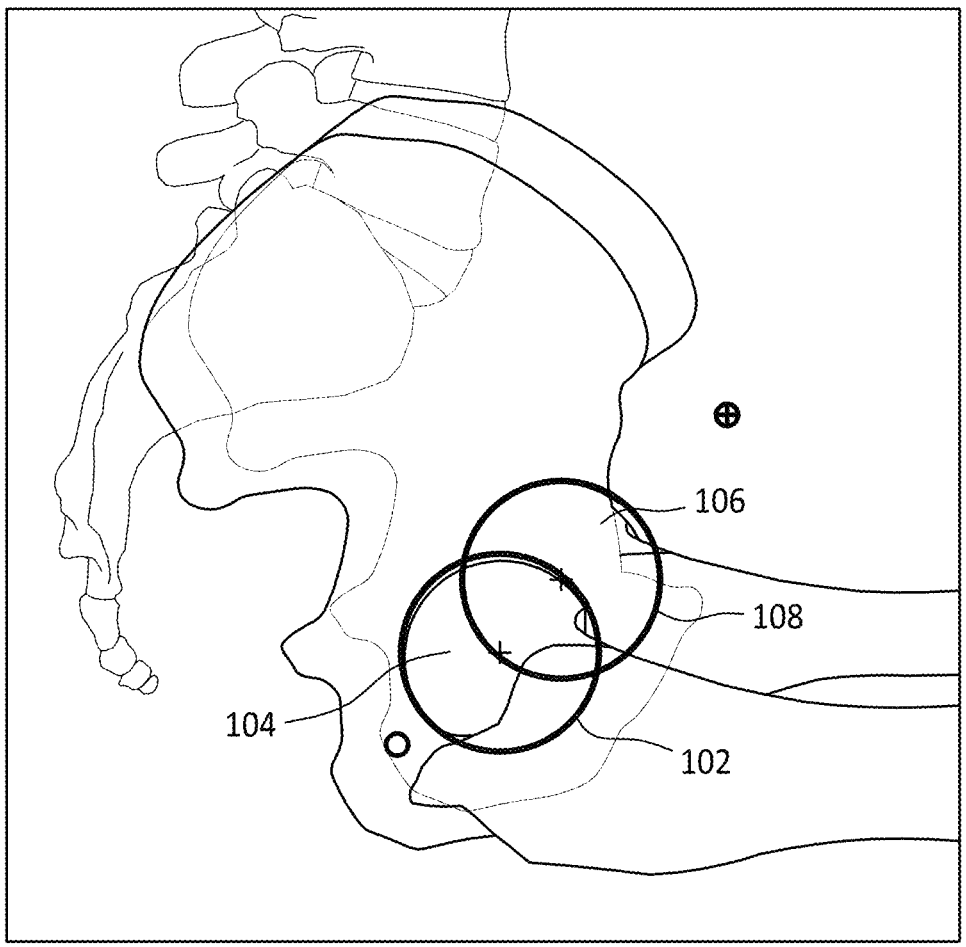
FIG. 7 is an exemplary preoperative lateral image of a patient's pelvic region when the patient is in a seated position. The figure depicts the step in which a circle is drawn around the other femoral head.

As explained in step 406 in FIG. 5 and illustrated in FIG. 6, the present invention directly calculates the SPT angle from the lateral image, by first digitally registering an anatomical landmark in the form of circle 102 around femoral head 104 in the preoperative image. The anatomical landmark can be manually or automatically digitally registered. In some embodiments, the center point of the femoral head is determined and/or digitally registered on the preoperative image rather than using a circle. Similarly, an embodiment may identify the center point of the acetabulum rather than relying on location of the femoral head.

In some embodiments, the lateral image is not an exact lateral image and as a result, the patient's femoral heads are not laterally aligned. In such an instance, as explained in step 408 in FIG. 5 and illustrated in FIG. 7, the center of the patient's other lateral head 106 or acetabulum is identified by an anatomical landmark, such as the center point or circle 108 depicted in FIG. 7. The midpoint between the center points of each femoral head becomes the vertex of the spinal tilt angle (see FIG. 9).

Figure 8:
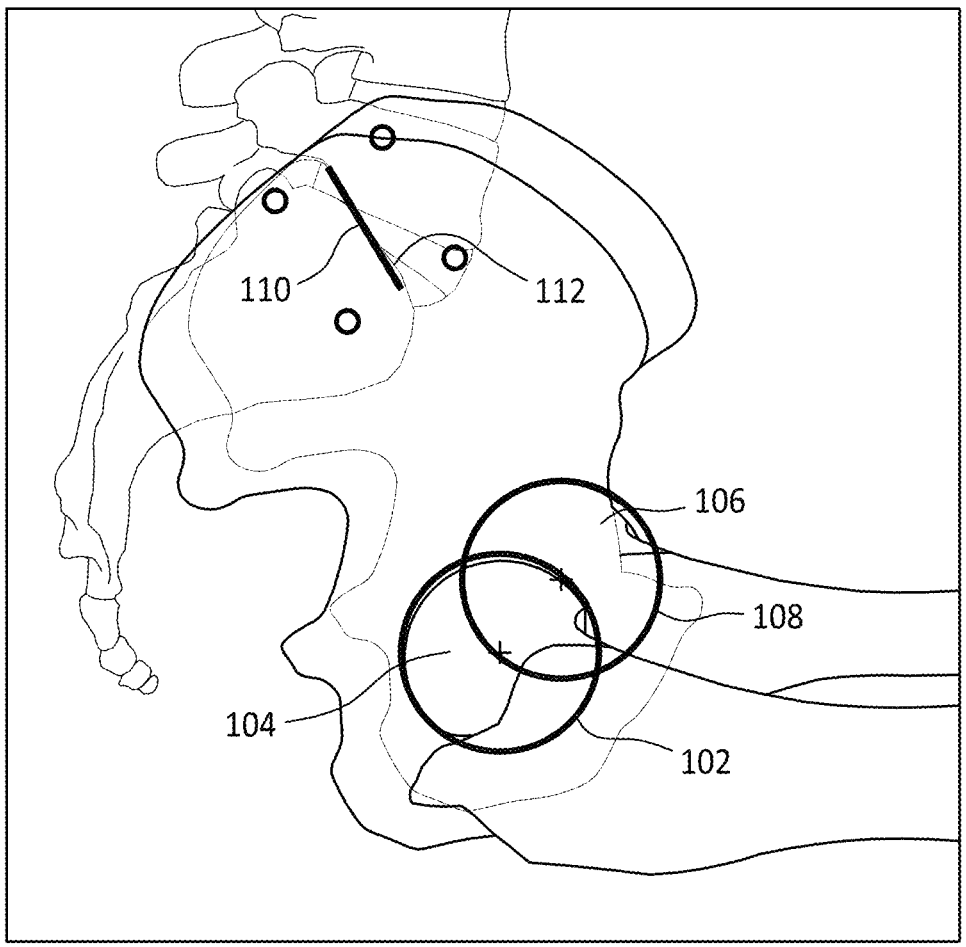
FIG. 8 is an exemplary preoperative lateral image of a patient's pelvic region when the patient is in a seated position. The figure depicts the step in which a line is drawn in relation to the sacrum.

The system then automatically or instructs a user to manually digitally register an anatomical landmark in relation to the sacrum at step 410. As shown in FIG. 8, the depicted anatomical landmark is line segment 110 outlining superior endplate 112 of the S1 vertebrae from the anterior to posterior border (i.e., from end to end). With the anatomical landmarks identified, calculation engine 206 can calculate the SPT angle at step 412. As previously noted, different vertebrae and different structural features of vertebrae may be used as the anatomical landmark, so long as appropriate correction factors are used. Regardless of which vertebral anatomical landmark is used, it should remain the same for the analyses of the other images to maintain precision.

In order to calculate the SPT angle in step 412, midpoint 114 of line segment 110 is identified and used as one of the endpoints for determining the SPT angle. In some embodiments, the midpoint of the sacral plate is visually determined without first outlining the sacrum with a line segment.

Line 116 extending from vertex 118 between the femoral heads to midpoint 114 of the sacrum line establishes a first vector defining the SPT angle. The system then digitally registers first neutral axis 120 extending vertically from vertex 118, which is the second vector defining the SPT angle. Calculation engine 206 can then use the two vectors to calculate the SPT angle.

Figure 9:
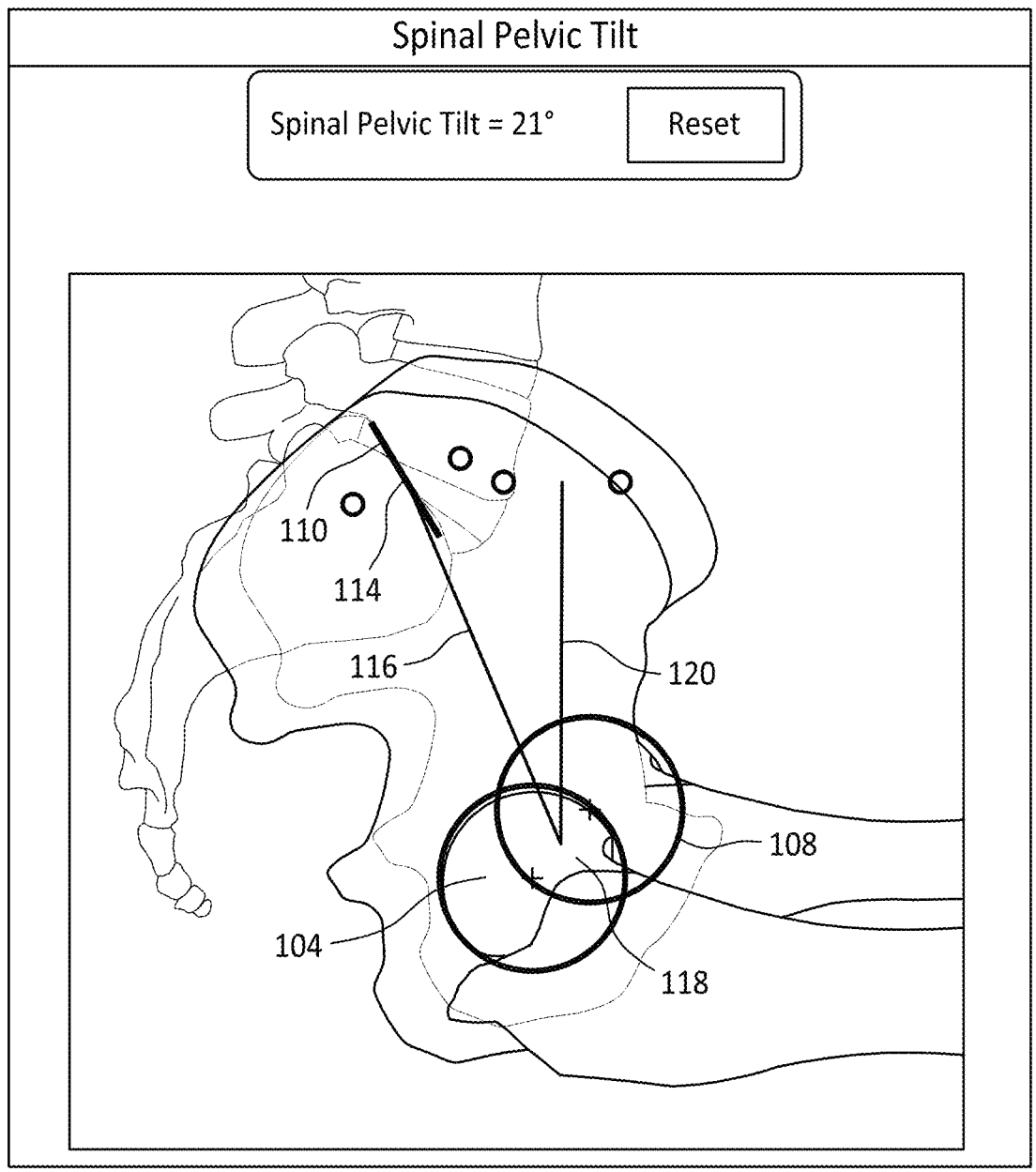
FIG. 9 is an exemplary preoperative lateral image of a patient's pelvic region when the patient is in a seated position. The figure depicts the step in which a first neutral axis line is drawn and the angle between the first neutral axis line and the sacrum line is calculated to identify the spinal pelvic tilt.
Figure 10:
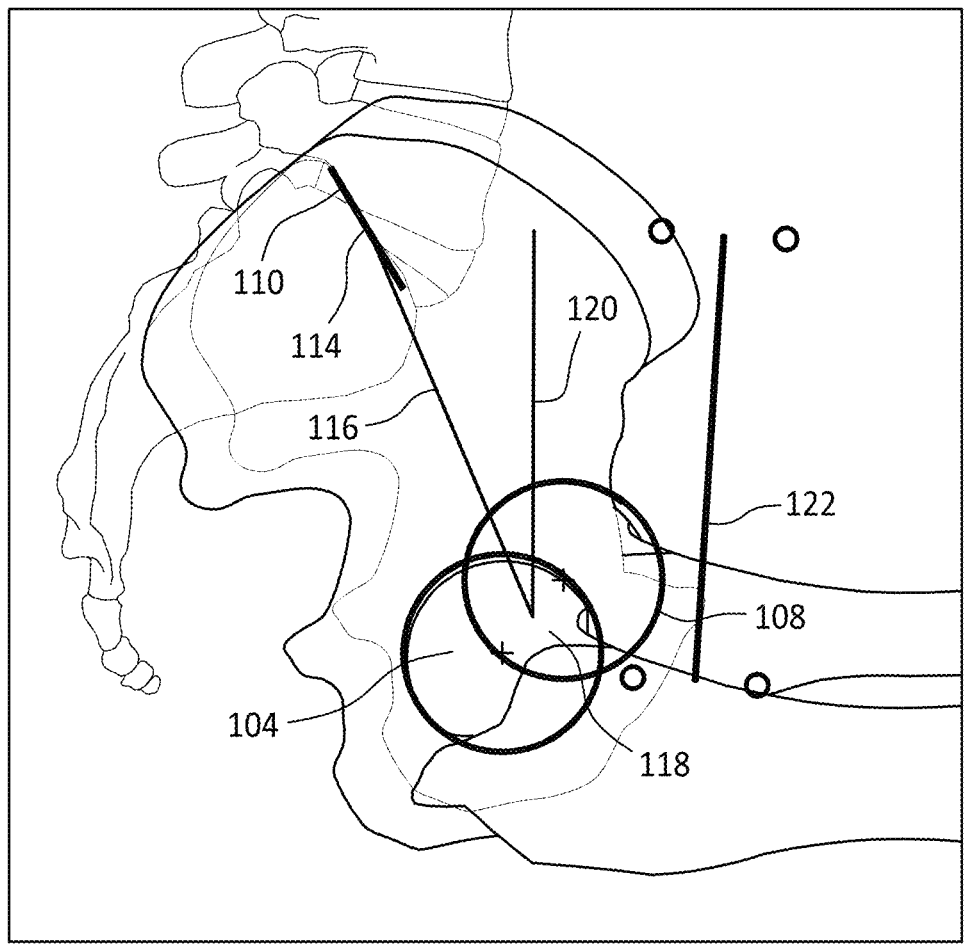
FIG. 10 is an exemplary preoperative lateral image of a patient's pelvic region when the patient is in a seated position. The figure depicts the step in which a line is drawn from the anterior superior iliac spine (ASIS) to the pubic symphysis.
Figure 11:
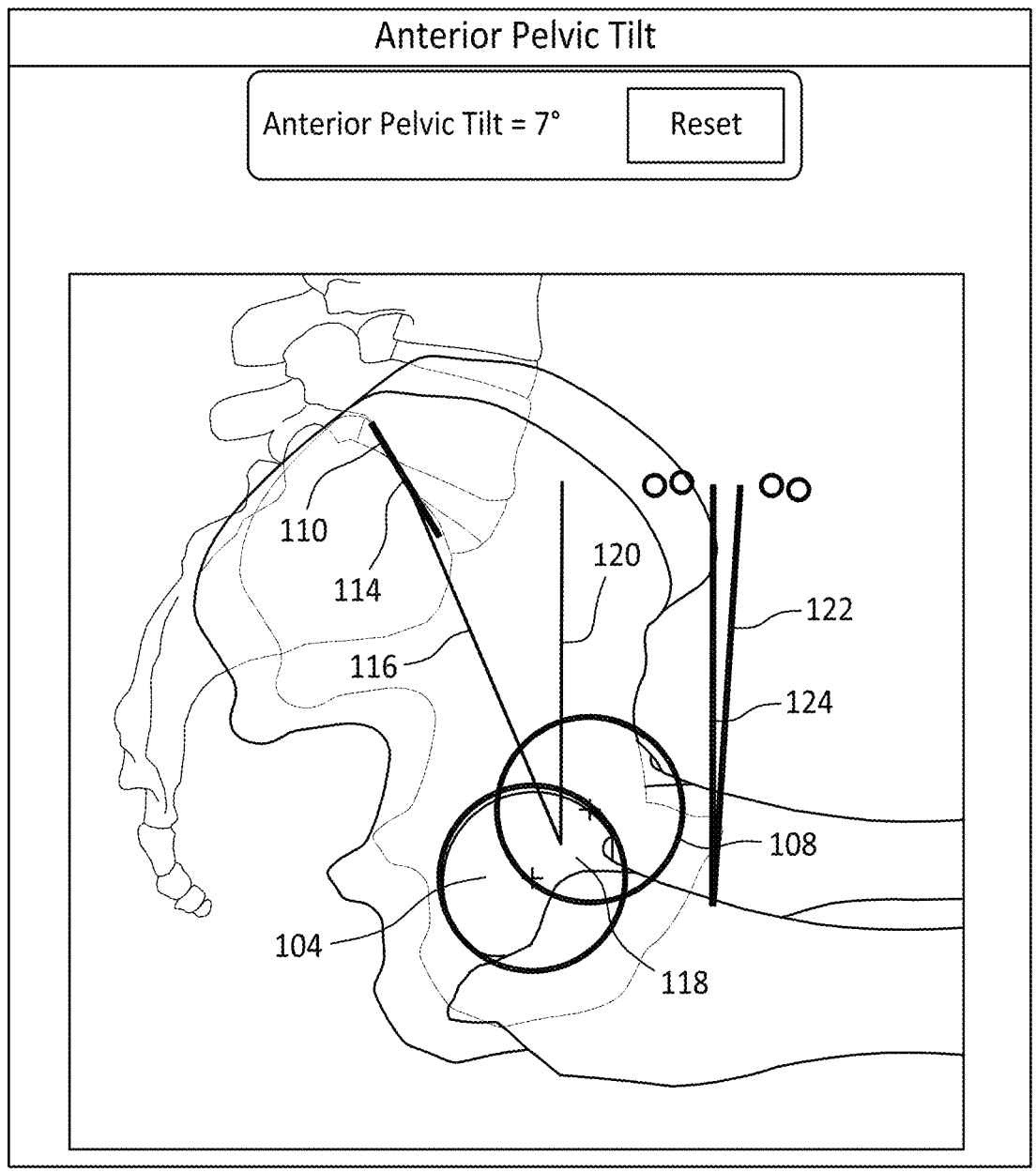
FIG. 11 is an exemplary preoperative lateral image of a patient's pelvic region when the patient is in a seated position. The figure depicts the step in which a second neutral axis line is drawn and the angle between the second neutral axis line and the ASIS line is calculated to identify the anterior pelvic tilt.
Figure 12:
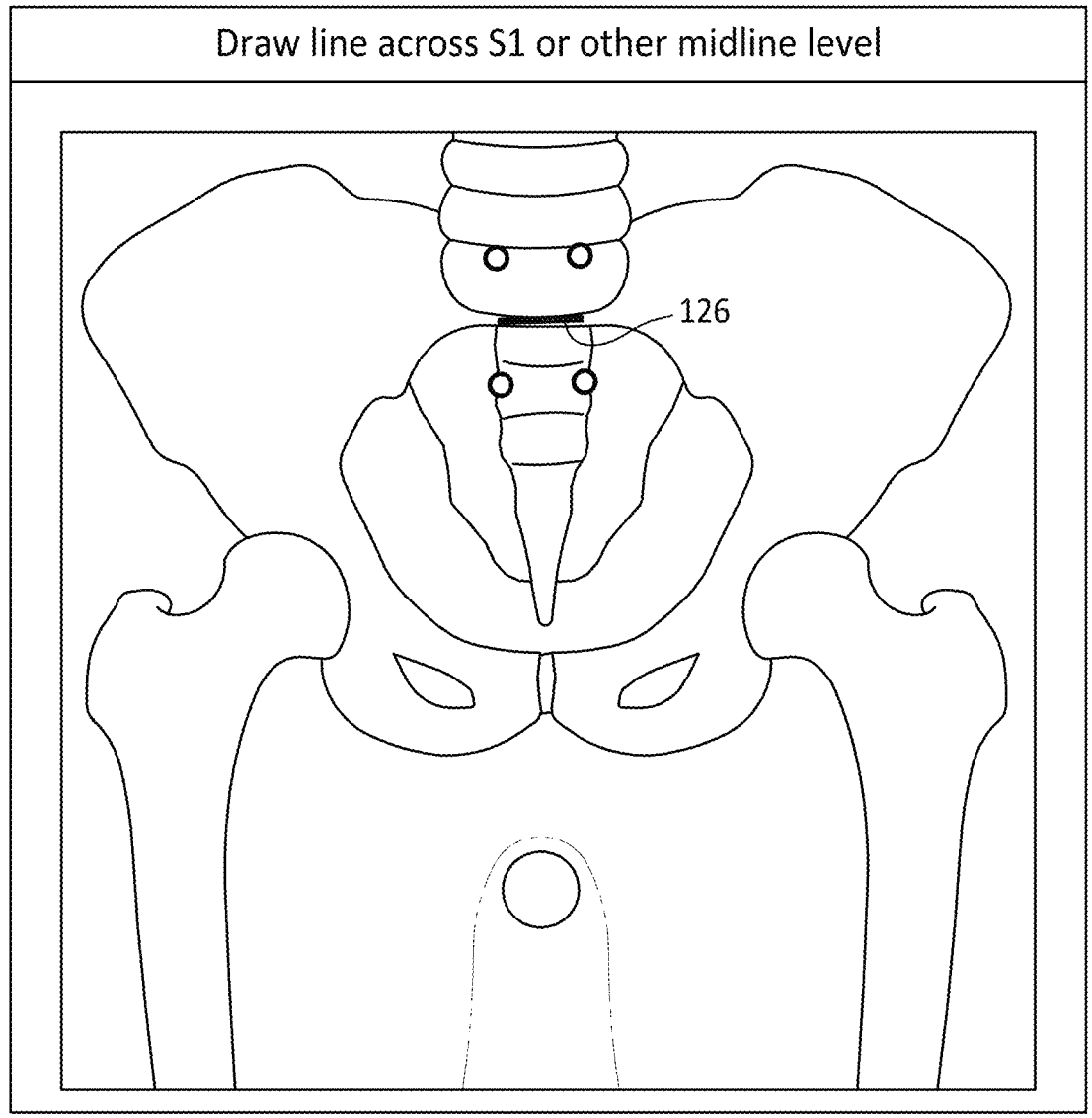
FIG. 12 is an exemplary preoperative supine anteroposterior image of a patient's pelvic region depicting the step in which a line is drawn across the S1 upper endplate.

Once the SPT angle is calculated, pelvic position display module 208 can then display the angle between the first and second vectors as depicted in FIG. 9 to visually convey the SPT angle when the patient is in the seated position. Alternatively, the system can forego the digital registration of one or both vectors and simply calculate the SPT angle between the two.

It should be noted that the first neutral axis is parallel to what would be a line normal to the Earth's surface, i.e., a line parallel to the direction of the force of gravity. In some embodiments, the preoperative images are first oriented/reoriented to ensure that the vertical neutral axis will align with a line normal to the Earth's surface. Alternatively, the imaging capturing system is initially oriented to ensure that the captured images will show the patient's anatomy in the intended orientation such that the vertical neutral axis will align with a line normal to the Earth's surface. In some embodiments, the user is provided with the option to manually rotate the preoperative image as needed to better capture the true orientation of a patient's pelvis in real time.

In some embodiments, the system further determines the sacral slope of the patient while in the seated position. Since determination of the SPT angle already requires a step of outlining the S1 endplate, the system could use this same anatomical landmark to easily calculate the sacral slope. To do so, image annotation module 204 digitally registers a horizontal line from the higher endpoint of the S1 endplate landmark. Calculation engine 206 can then calculate sacral slope—the angle between the line outlining the S1 endplate and the horizontal line. In some embodiments, the system displays the sacral slope angle to the user. In some embodiments, the sacral slope is calculated but not displayed. Ultimately, the angle of the sacral slope plus the SPT angle provides the pelvic incidence, which is consistent in every anatomical position.

In some embodiments, the sacral slope is based on the endplate of the S1 vertebrae. However, the alternative vertebrae can be used, including but not limited to other sacral vertebrae and lumbar vertebrae. In addition, structural features of the vertebrae may be relied upon instead of the endplates. As previously explained, regardless of which vertebral anatomical landmark is used, it should remain the same for the analyses of the other images to maintain precision.

In some embodiments, the pelvic tilt from lateral images is always determined using the sacral slope. The sacral slope does not rely on the femoral heads which can be difficult to accurately identify in medical imaging. In addition, the sacral slope changes at a 1:1 rate with the SPT angle based on pelvic incidence. Thus, measuring the sacral slope is an alternative and easier approach to determine pelvic tilt.

In some embodiments, the system further determines an anterior pelvic tilt (APT) angle to provide greater clarity in the display of the patient's pelvis in the implant analysis interface depicted in FIG. 20. To determine the APT angle, the system automatically, or instructs a user to manually perform the following steps. First, as explained in step 414 in FIG. 5 and illustrated in FIG. 10, image annotation module 204 digitally registers line 122 from the anterior superior iliac spine (ASIS) to the superior point on the pubic symphysis (see FIG. 5). Then at step 416 second neutral axis 124 is digitally registered vertically from the superior point on the pubic symphysis (see FIG. 11). Calculation engine 206 determines the APT angle between second neutral axis 124 and the line 122 extending between the ASIS and the superior point on the pubic symphysis. Similar to the determination of the SPT angle, the system can forego the digital registration of one or both lines and simply calculate the APT angle between the two. In some embodiments, pelvic position display module 208 displays the APT angle to the user on the user interface as exemplified in FIG. 11.

The sign (+ or -) of the APT angle is dependent on whether the ASIS is closer or further to the sacrum (or center of femoral heads) than the pubic symphysis. If ASIS is closer the angle is negative, if ASIS is further the angle is positive. In addition, the preoperative image can be either left or right for either body side. A check needs to be performed prior to calculating the angle. If the pubic symphysis 'X' value is less than the femoral head center the image is left at the forefront. If the pubic symphysis 'X' value is greater than the femoral head center the image is right at the forefront.

Supine Pelvic Tilt

As previously explained, in the vast majority of instances, an AP image is captured when the patient is in a supine position. Thus, while a lateral image can be used in accordance with the steps above or in accordance with the steps corresponding to the determination of a sacral slope (described in the standing pelvic tilt section), this section will focus on the steps for determining the SPT angle while the patient is in a supine position using an AP image. The steps are described in the flowchart of FIG. 5 and illustrated in FIGS. 12-14.

Figure 13:
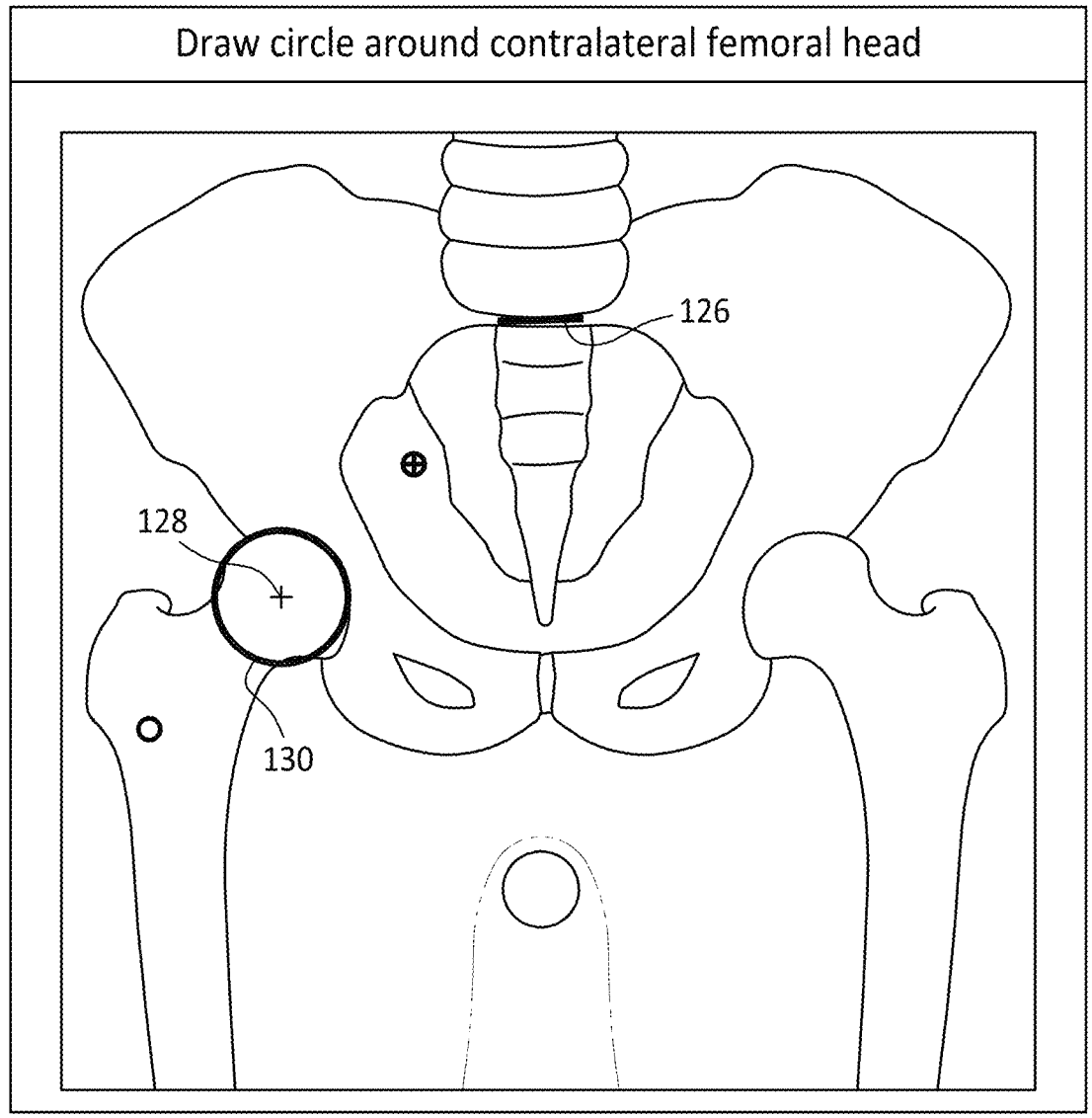
FIG. 13 is an exemplary preoperative supine anteroposterior image of a patient's pelvic region depicting the step in which a circle is drawn around the contralateral femoral head.
Figure 14:
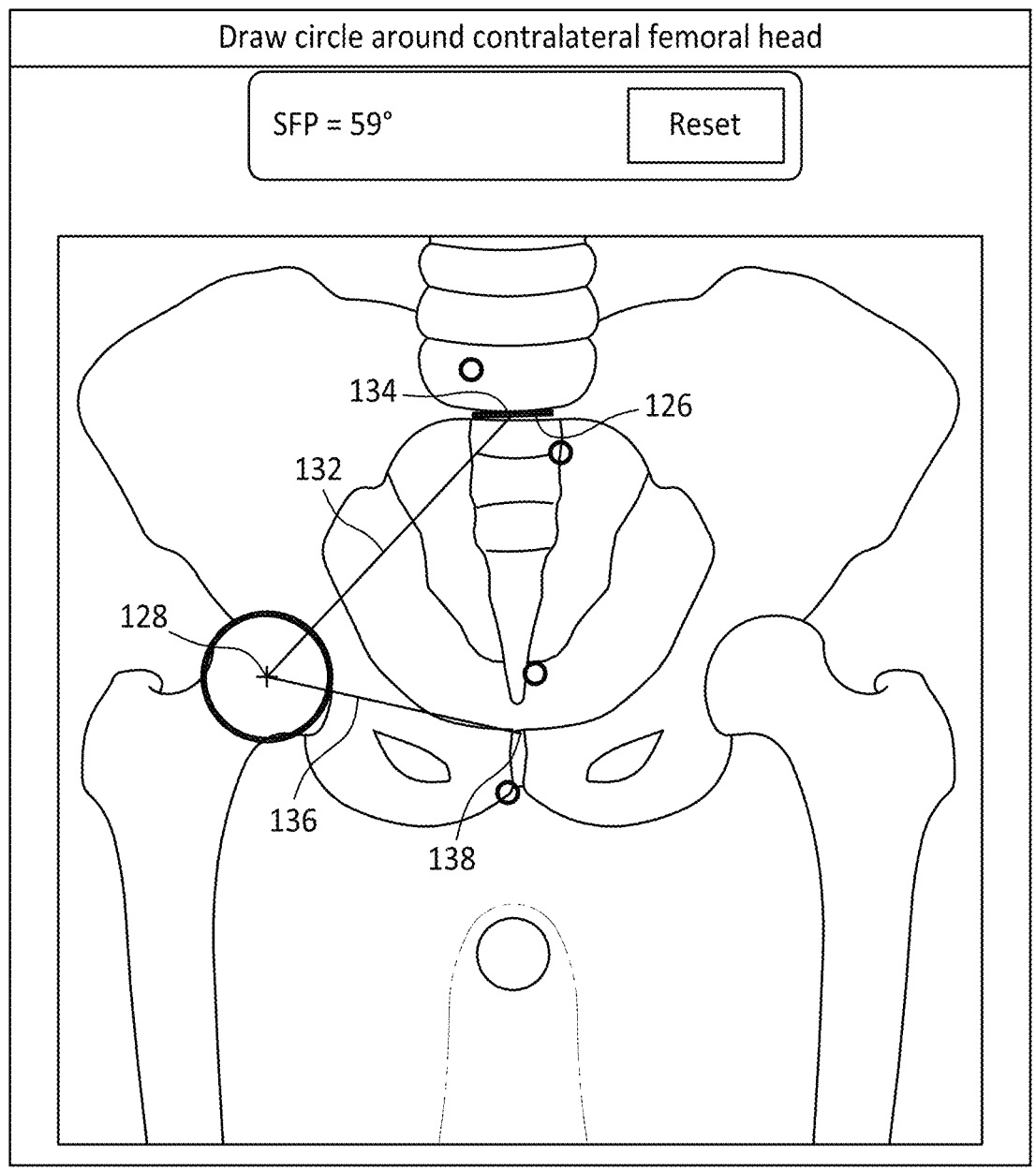
FIG. 14 is an exemplary preoperative supine anteroposterior image of a patient's pelvic region depicting the step in which the sacral femoral pubic angle is calculated.

As shown in FIG. 5, image acquisition module 202 acquires a preoperative supine AP image at step 418. Image annotation module 204 then digitally registers line 126 across the upper endplate of the S1 vertebrae (see FIG. 12) at step 420. At step 422, image annotation module 204 digitally registers center point 128 of the contralateral femoral head using circle 130, which is illustrated in FIG. 13. Center point 128 of the femoral head is identified as the vertex of the SFP angle. First line 132 extends between vertex 128 and midpoint 134 of the S1 vertebrae line 126 and second line 136 extends between vertex 128 and superior point 138 on pubic symphysis. The angle between the two lines 132 and 136 is the SFP angle. Calculation engine 206 determines the SFP angle at step 424 and pelvic position display module 208 displays the angle as shown in FIG. 14. Having determined the SFP angle, the system then calculates the SPT angle based on Equation 1:

$$SPT_{angle} = SFP_{constant} - SFP_{angle} \qquad (Eq.\ 1)$$

For most patients, the SFP constant is set to 75, however, as previously explained a patient specific SFP constant can be determined by comparing the preoperative AP standing image and the preoperative lateral standing image, which will be described in the Standing pelvic tilt section below. Furthermore, an embodiment of the present invention can rely on different vertebrae for the anatomical landmark in step 420, including but not limited to any of the sacral and lumbar vertebrae. However, the use of different vertebrae will result in different SFP constants and the vertebral anatomical landmark point should remain constant with the analyses of the other images.

In some embodiments, the step of identifying or digitally registering the vertex of the SFP angle includes identifying (manually through an end user or automatically using software) the non-operative femoral head. Often the operative femoral head requires operation because its location or anatomical structure has been compromised. Reliance on the operative head would therefore likely result in a vertex location (and thus an SFP angle) that is not a true representation of the patient's original uncompromised anatomy. For that reason, the vertex is identified in relation to the non-operative femoral head, which in most cases will provide a more accurate representation of the patient's true original anatomy and produce better outcomes. Thus, some embodiments include a user-input step in which the user identifies which hip is the operative hip and/or which hip is the non-operative hip.

In some embodiments, the position of superior point on pubic symphysis is estimated based on the 'Y' coordinate of center of femoral head circle, and 'X' coordinate of the midpoint of the vertebrae line. In addition, digitally registering the superior point on the pubic symphysis, like other anatomical landmarks, may be accomplished through image recognition software or through user input.

As mentioned above, the present invention may determine the patient's pelvic tilt while the patient is in a supine position using a lateral image of the pelvis. This can be accomplished by calculating the SPT angle as describe in the Seated pelvic tilt section and/or the pelvic tilt can be determined based on the sacral slope as will be described in the Standing pelvic tilt section.

Standing Pelvic Tilt

To reiterate, this section describes the steps for determining the pelvic tilt from a lateral image using the sacral slope. The sacral slope does not rely on the femoral heads which can be difficult to accurately identify in medical imaging. In addition, the sacral slope changes at a 1:1 rate with the SPT angle based on pelvic incidence. Thus, measuring the sacral slope is an alternative and easier approach to determine pelvic tilt if the pelvic incidence is known. However, the pelvic tilt could be determined based on calculating the SPT angle as described in the Seated pelvic tilt section.

This section also describes an embodiment including steps for (1) determining the pelvic tilt of a patient when in a standing position using the sacral slope as determined from a lateral image and (2) determining the SFP angle as determined from an AP image when the patient is in a standing position, and (3) calculating the patient specific SFP constant. However, some embodiments only use a lateral or only an AP image to determine the pelvic tilt of the patient when in a standing position.

Figure 15:
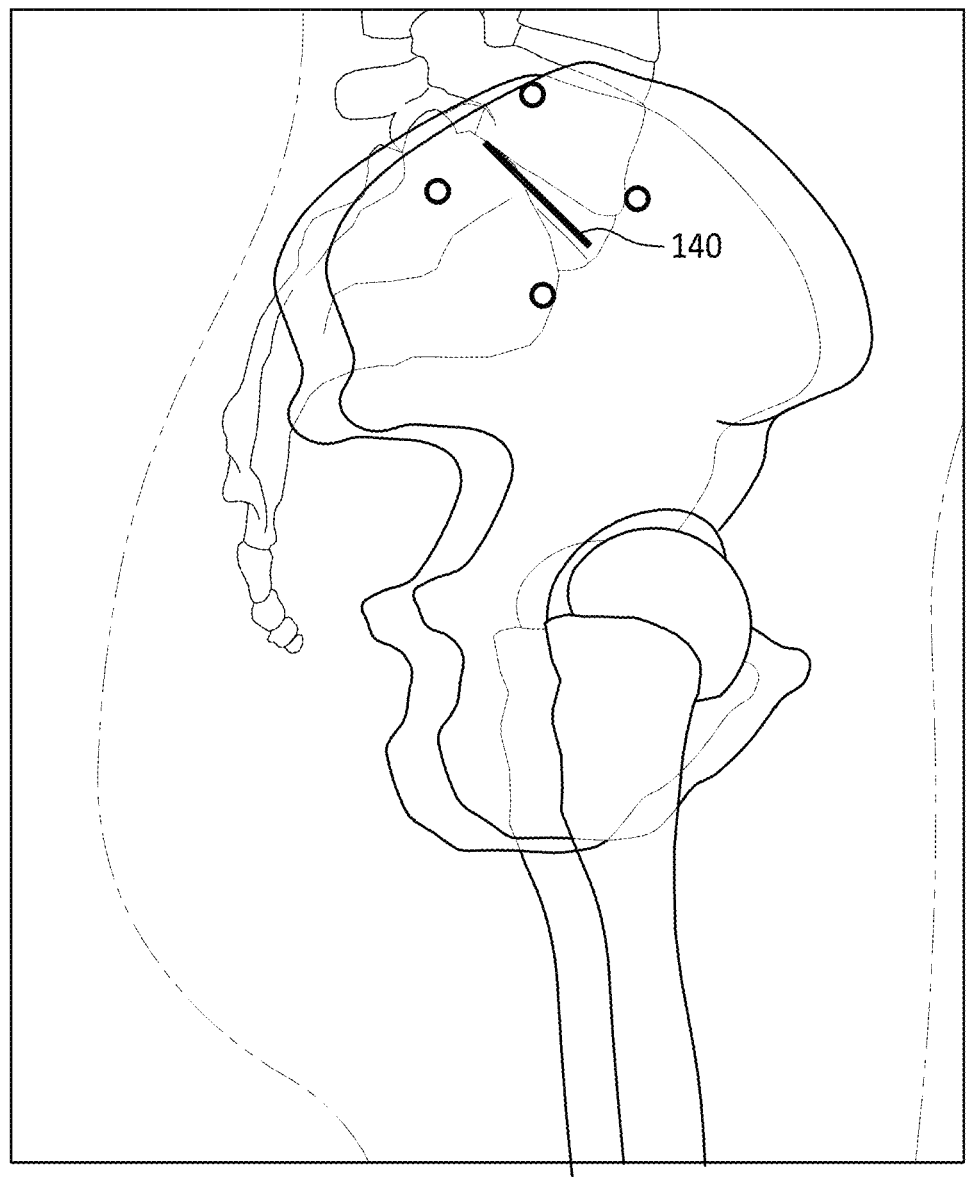
FIG. 15 is an exemplary preoperative standing anteroposterior image of a patient's pelvic region depicting the step in which a line is drawn across the S1 upper endplate.
Figure 16:
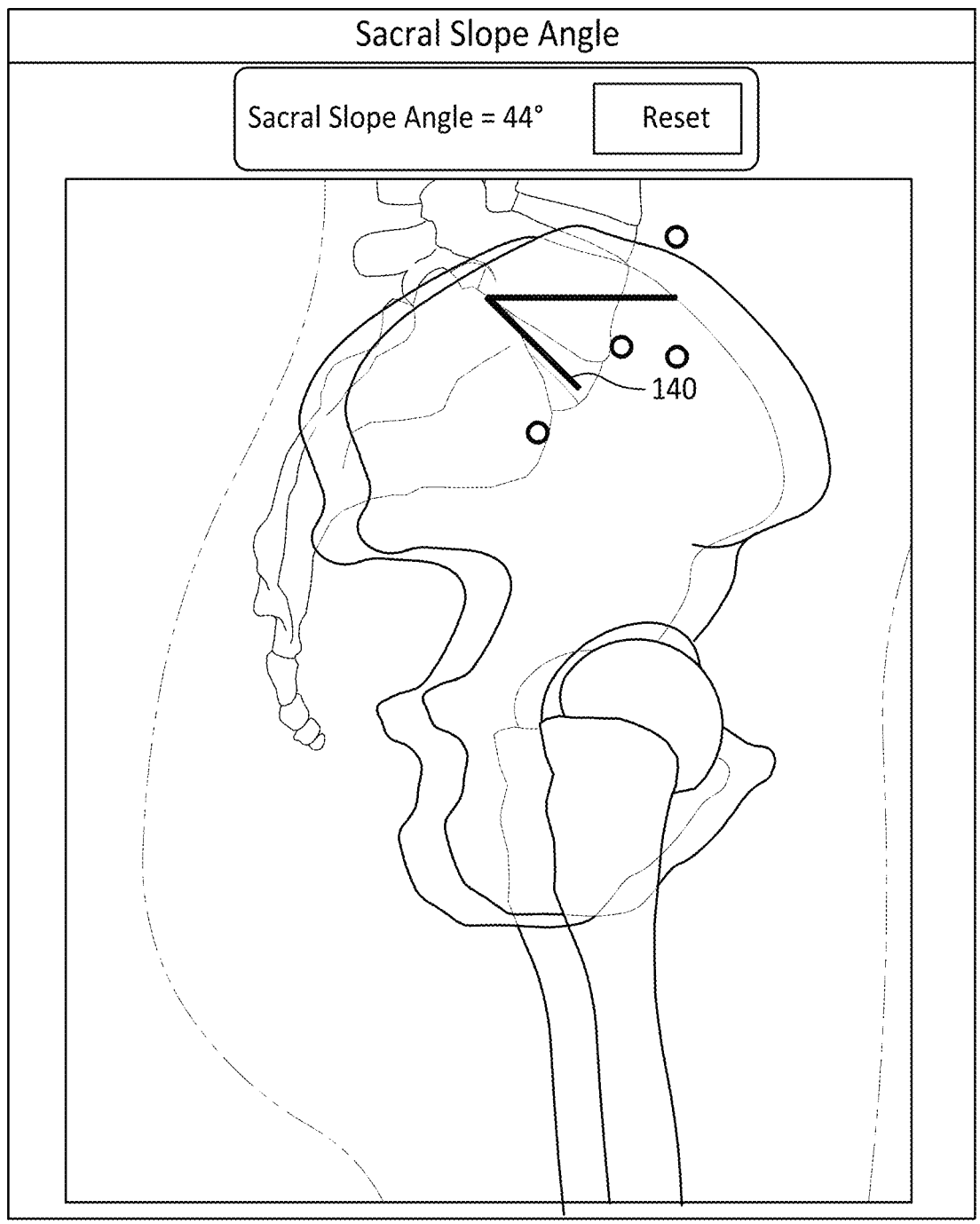
FIG. 16 is an exemplary preoperative standing anteroposterior image of a patient's pelvic region depicting the step in which a horizontal axis line is drawn from a posterior point on the S1 upper endplate to calculate the sacral slope.
Figure 17:
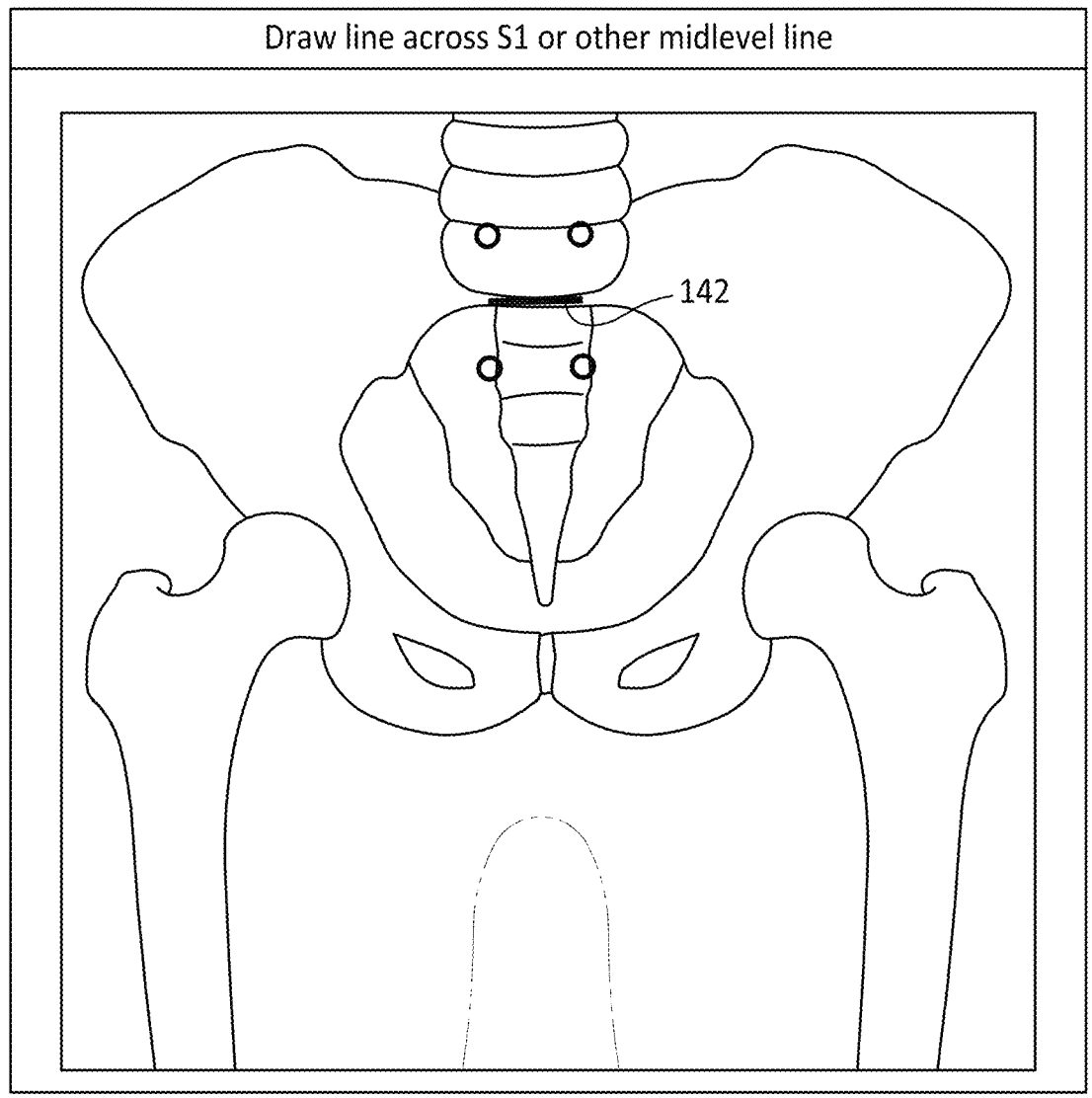
FIG. 17 is an exemplary preoperative standing anteroposterior image of a patient's pelvic region depicting the step in which a line is drawn across the S1 upper endplate.

Referring now to FIGS. 5 and 15-16, image acquisition module 202 acquires a preoperative lateral standing image at step 426. Image annotation module 204 digitally registers line 140 from the anterior to posterior border of the S1 endplate at step 428, which is illustrated in FIG. 15. Image annotation module 204 can then digitally registers horizontal line 142 from the higher endpoint of the S1 endplate landmark 140. Calculation engine 206 calculates the angle between line 140 outlining the sacral endplate and horizontal line 142 and pelvic position display module 208 displays the sacral slope at step 430. The display of the sacral slope angle is illustrated in FIG. 16.

While the described embodiment determines the sacral slope using the endplate of the S1 vertebrae, alternative vertebrae can be used, including but not limited to other sacral vertebrae and lumbar vertebrae. In addition, structural features of the vertebrae may be relied upon instead of the endplates. However, the vertebral anatomical landmarks should coincide with those used in the analyses of the other images.

Some embodiments further include steps for determining the SFP angle from an AP view when the patient is in a standing position. The reason for using a lateral image and an AP image is to calculate a patient specific SFP constant rather than relying on the less precise value of 75. The value of the SFP constant of the patient remains constant regardless of the patient's anatomical position and is valuable in producing more accurate data when the intraoperative image is an AP image.

Figure 18:
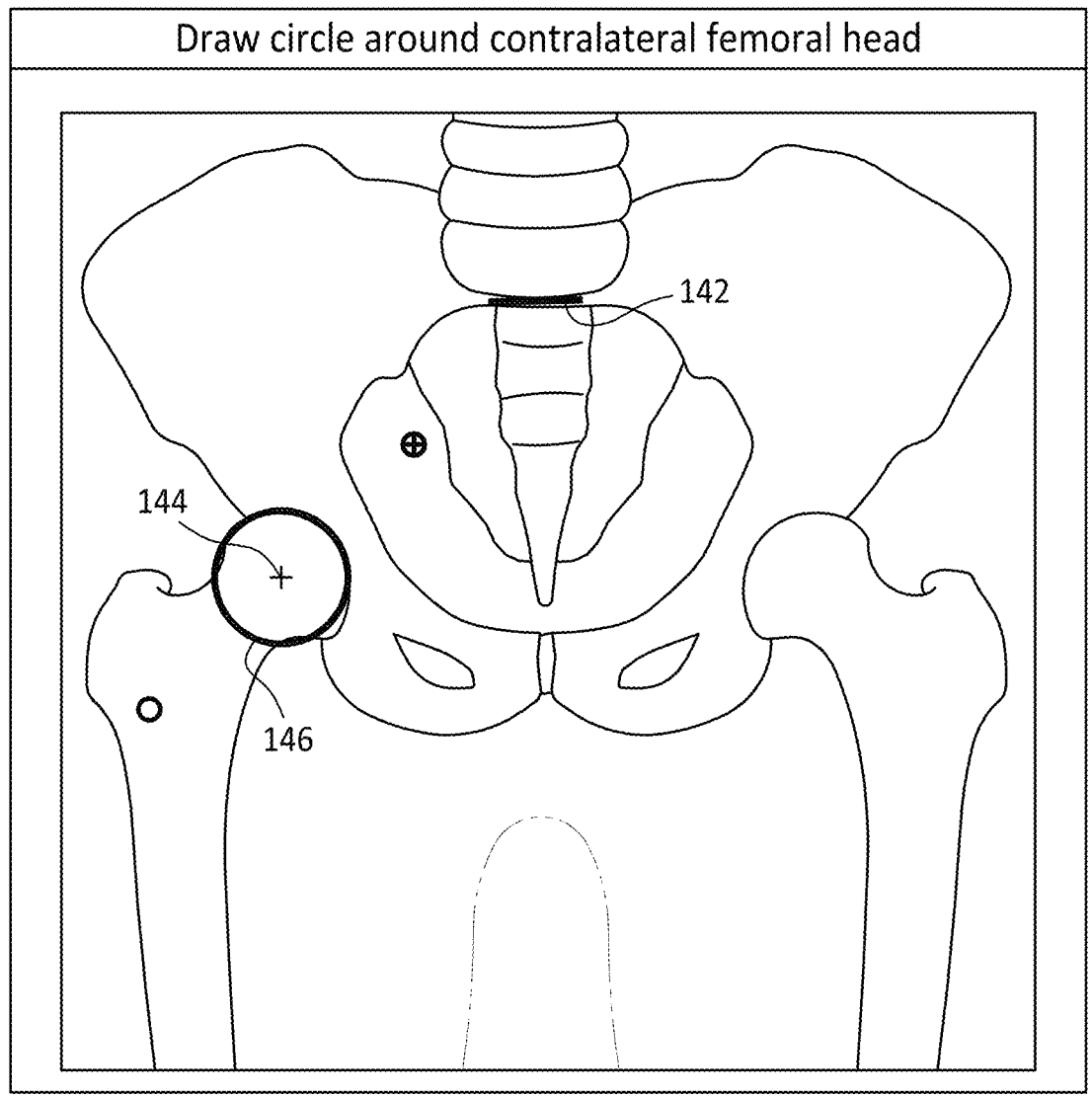
FIG. 18 is an exemplary preoperative standing anteroposterior image of a patient's pelvic region depicting the step in which a circle is drawn around the contralateral femoral head.
Figure 19:
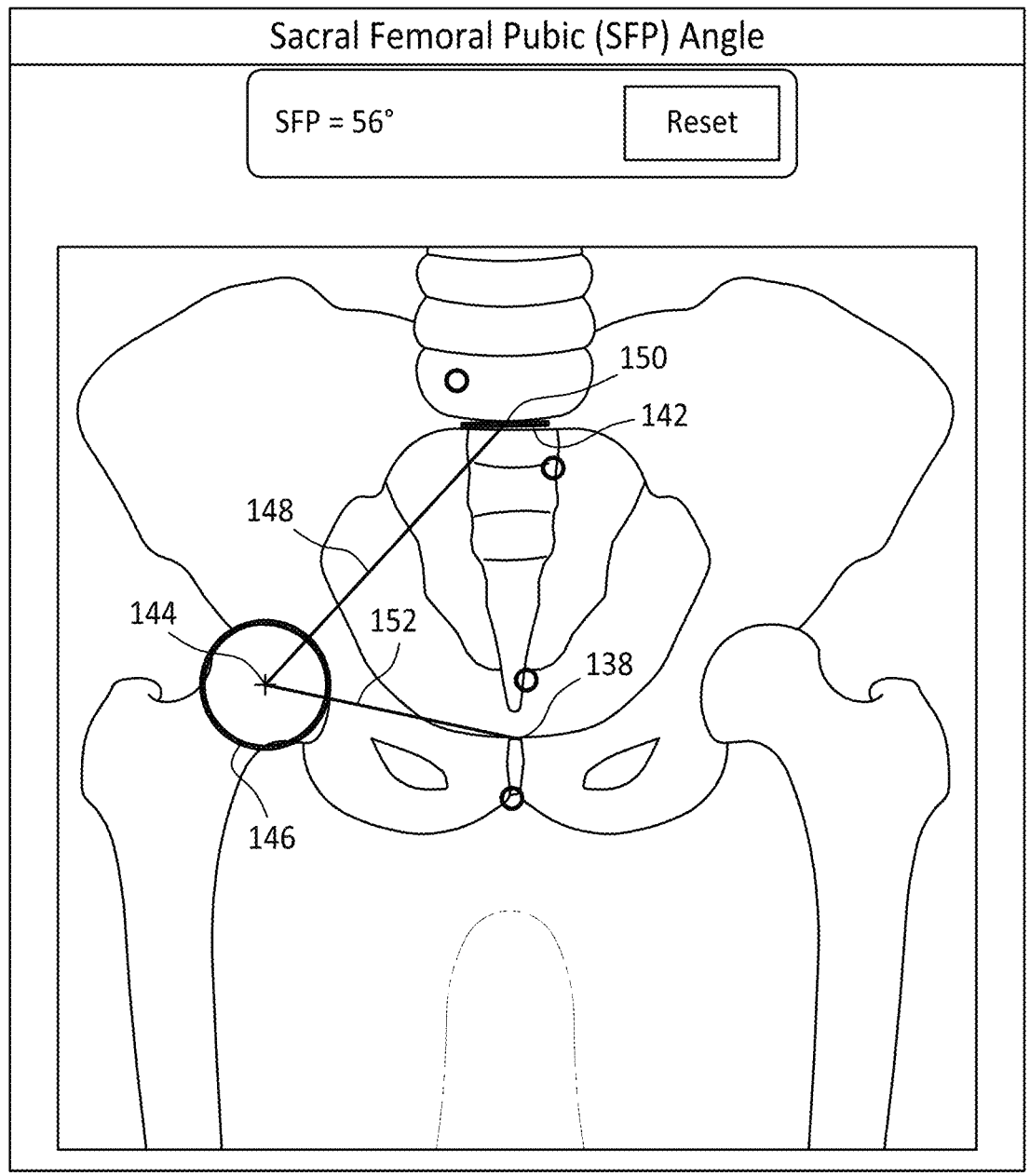
FIG. 19 is an exemplary preoperative standing anteroposterior image of a patient's pelvic region depicting the step in which the sacral femoral pubic angle is calculated.

The steps for determining the SFP angle while the patient is in a standing position using an AP image are the same as those described in 420-424 in FIG. 5. Referring to FIGS. 5 and 17-19, image acquisition module 202 acquires a preoperative AP image of a patient's pelvic region when the patient is in a standing position at step 432. Image annotation module 204 then digitally registers line 142 across the upper endplate of the S1 vertebrae (see FIG. 17) at step 434. At step 436, image annotation module 204 digitally registers center point 144 using circle 146 around the contralateral femoral head, which is illustrated in FIG. 18. Center point 144 of the femoral head is identified as the vertex of the SFP angle. First line 148 extends between vertex 144 and midpoint 150 of the S1 vertebrae line and second line 152 extends between vertex 144 and superior point 154 on the pubic symphysis. The angle between the two lines is the SFP angle. Calculation engine 206 determines the SFP angle at step 438 and pelvic position display module 208 displays the angle as shown in FIG. 19.

Having determined the SFP angle form the AP image, and knowing the SPT angle from the lateral image, the system then calculates SFP constant using Equation 1. Some embodiments use the patient specific SFP constant to more precisely calculate the pelvic tilt of the patient from the supine AP image.

Again, the vertebral anatomical landmark can be any of the sacral and lumbar vertebrae. However, the use of a different vertebrae will result in a different SFP constant. Thus, the same vertebral anatomical landmark must be used in each of the steps to ensure that the SFP constant remains accurate.

While the specification describes an embodiment in which an AP and lateral image are captured while the patient is in the standing position to calculate a patient specific SFP constant, other embodiments can use the seated or supine positions to capture both lateral and AP images to calculate the patient specific SFP constant.

Preoperative Analysis

The preoperative analysis is important because different parameters in different functional positions may present different dislocation risks. For example, consider that a standing patient will generally dislocate to the anterior, and therefore more anteversion in a standing position presents additional risk. The flex seated position on the other hand presents more risk of a posterior dislocation. Therefore, it is important to see how the risk in each position changes with the orientation/position of the acetabular cup component.

Generally, for the seated position, the safe zone is an anteversion value above 19 degrees, a medium risk zone is an anteversion value between 10 and 19 degrees, and a high-risk zone is an anteversion value less than 10 degrees. For the standing position, the safe zone is an anteversion value between 10 and 25 degrees, the medium risk zone is an anteversion value between 25 and 35 degrees, and the high-risk zone is an anteversion value less than 10 degrees and greater than 35 degrees. The system uses these values to assess the dislocation risk in the preoperative analysis. In some embodiments, the values that define the risk zones can be adjusted by a user.

Figure 20A:
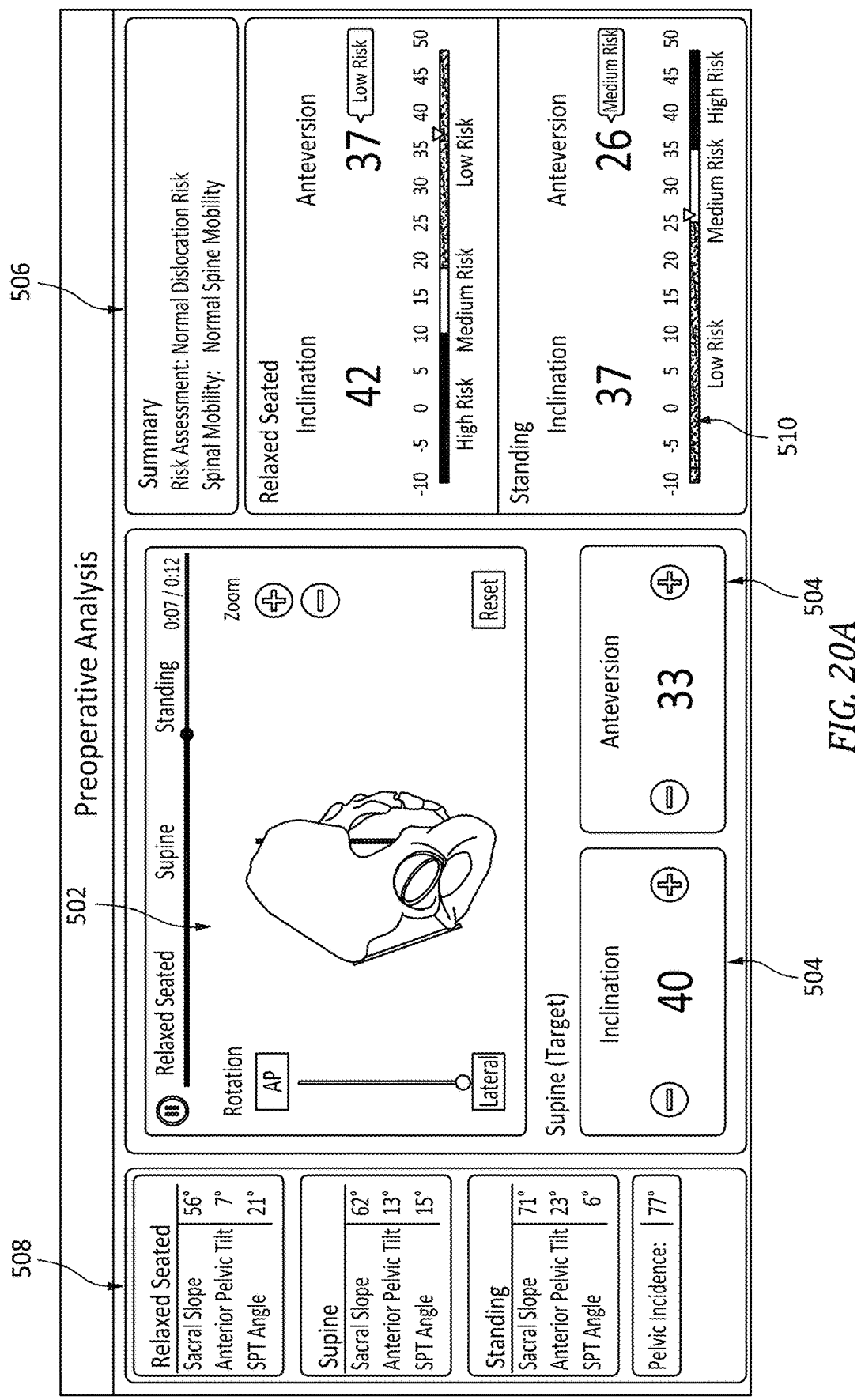
FIG. 20A is an embodiment of a graphic display of the hip dislocation risk in a standing, seated, and lying orientation based on preoperative analysis.

Following the determinations of the patient's pelvic tilt data in the seated, supine, and standing positions, the system displays the pelvic position analysis data to an end user (typically the orthopedic surgeon) at step 440 to allow the user to determine the preferred orientation of the acetabular cup component of the implant. An example of how the preoperative pelvic position analysis data can be conveyed is found in FIG. 20. As shown in FIG. 20A, an embodiment of display 500 includes the data associated with pelvic tilt for each anatomical position in a series of boxes on the left-hand side of the screen, which is generally identified by reference numeral 508.

Figure 20B:
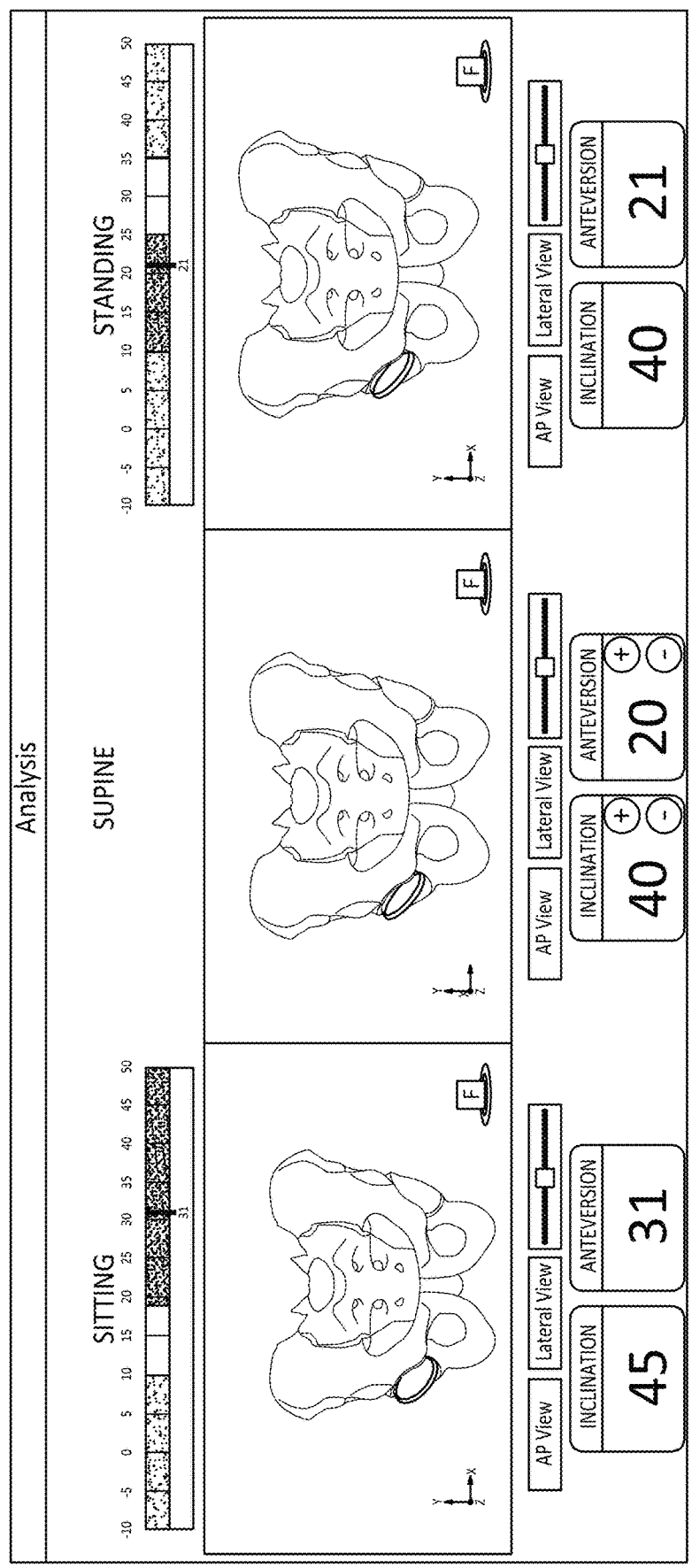
FIG. 20B is an embodiment of a graphic display of the hip dislocation risk in a standing, seated, and lying orientation based on preoperative analysis.
Figure 20C:
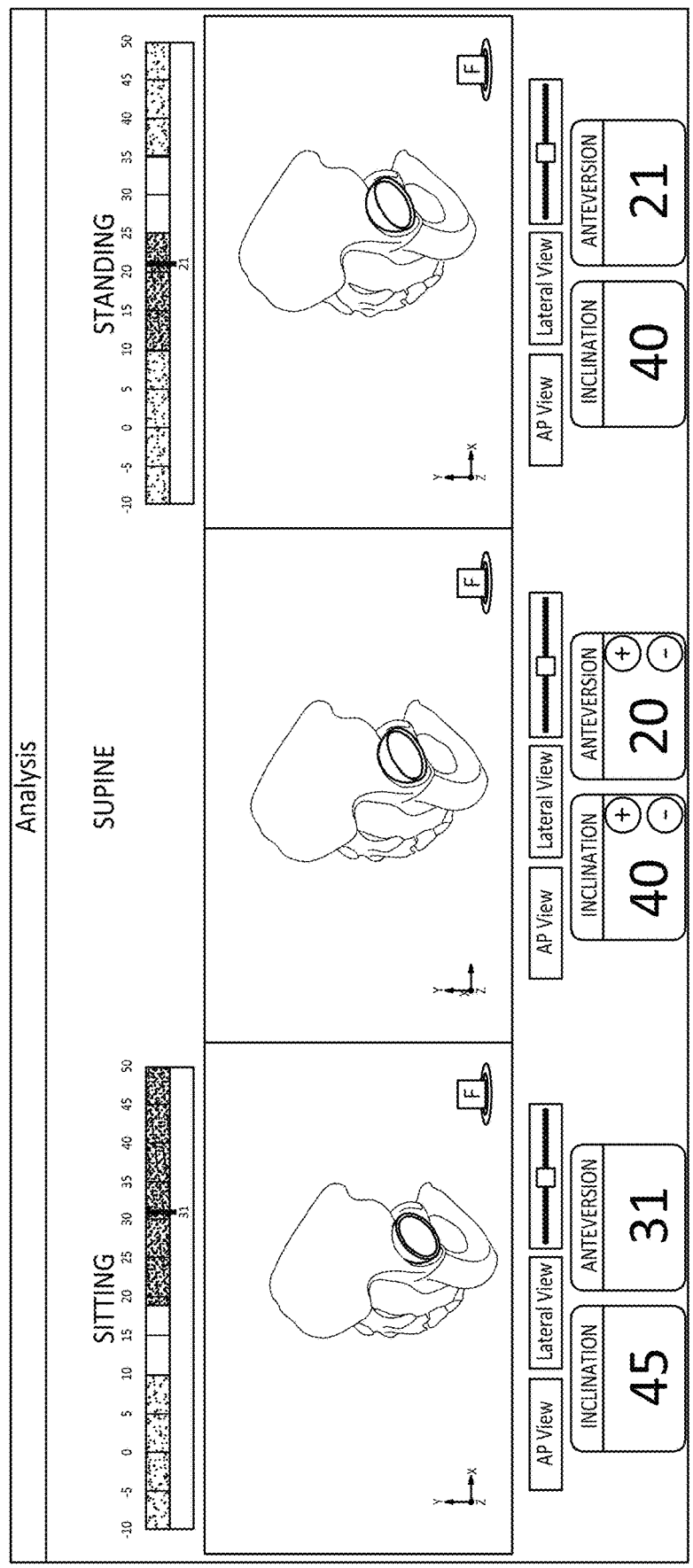
FIG. 20C is an embodiment of a graphic display of the hip dislocation risk in a standing, seated, and lying orientation based on preoperative analysis.

Display 500 also preferably displays one or more 3-dimensional images of the patient's pelvis, or a representative pelvis, with a digital representation of an acetabular cup component residing in the acetabulum in display window 502. Preferably, display 500 allows a user to see the pelvis in each anatomical position: seated, standing, and lying. This can be done in a video type format as depicted in FIG. 20A or in a side-by-side manner as shown in FIGS. 20B-20C.

Moreover, the end user is provided with the ability to adjust the location and orientation of the acetabular cup in each representative image using graphic interfaces 504 (depicted as "+" and "−" buttons) to alter the anteversion and inclination data of the acetabular cup component. The inclination and anteversion can be adjusted in both the positive and negative directions.

The supine position is the preferred modifiable position because this is the position in which the patient resides during surgery. Thus, the surgeon will have a clear understanding of how the surgeon's modification of the acetabular cup component during surgery will impact the patient's dislocation risk after the surgery is complete and especially when the patient is in the higher risk positions—sitting and standing.

In some embodiments, the supine anteversion and inclination values are set to default values. Preferably the default resides within the Lewinnek safe zone. The exemplary depicted embodiment uses a default anteversion of 20 degrees and a default inclination angle of 40 degrees. In some embodiments, the predetermined supine anteversion value is initially set to a value between 20 and 30 degrees.

Based on the patient's pelvic tilt and the inclination and anteversion angles of the representative cup, the system calculates and displays the dislocation risk of the prosthetic hip when the patient is seated, standing, and lying. The risk can be displayed in summary box 506 and/or provided in a graphic representation, such as tilt bars 510.

In some embodiments, the risk summary box 506 is based upon the configured range parameters for the minimum and maximum anteversion and spinal mobility. If the relaxed seated anteversion is less than a known minimum safe anteversion (configurable) and the standing anteversion is greater than a known maximum safe anteversion (configurable), then the system displays "Risk Assessment: Anterior and Posterior Dislocation Risk." If relaxed seated anteversion is less than a known minimum safe anteversion then the system displays "Risk Assessment: Posterior Dislocation Risk." If seated anteversion is greater than the known maximum safe anteversion then the system displays "Risk Assessment: Anterior Dislocation Risk." Otherwise, the system displays "Normal Dislocation Risk"

If the preoperative sacral slope in the seated position minus the preoperative sacral slope in the standing position is less than spinal mobility threshold value (configurable) then the system displays "Spinal Mobility: Decreased Spinal Mobility." Otherwise, the system displays "Spinal Mobility: Normal Spine Mobility."

In some embodiments, tilt bars 510 are correspond to the anteversion value of the acetabular cup component. In an embodiment, tilt bars 510 will have a red section to indicate zones of high risk, a yellow section to indicates zones of medium risk, and a green section to indicate a safe zone. Thus, a cup position having an anteversion value that falls in the high risk/red section is in danger of dislocation. The dislocation risk is less in the medium risk/yellow section, but still concerning, and finally, the safest/green section is the ideal section.

Preferably display 500 includes both a quantitative measurement of the anteversion and inclination values for the various anatomic locations. Some embodiments also include qualitative indicators (colors to identify a safe zone, a medium dislocation risk zone, and a high dislocation risk zone) to convey the risk of dislocation when the patient is in various anatomical positions.

In order to properly convey how modification of the inclination and anteversion of the acetabular cup component in one of the anatomical positions alters the dislocation risk to the patient in other anatomical positions, the system employs the following equations:

$$\text{Anteversion}_{Sitting} = \text{Anteversion}_{Supine} + (\text{SPT}_{Supine} - \text{SPT}_{Sitting}) * \text{Ant}_{Co} \quad \text{(Eq. 2)}$$

$$\text{Inclination}_{Sitting} = \text{Inclination}_{Supine} + (\text{SPT}_{Supine} - \text{SPT}_{Sitting}) * \text{Inc}_{Co} \quad \text{(Eq. 3)}$$

$$\text{Anteversion}_{Standing} = \text{Anteversion}_{Supine} + (\text{SPT}_{Supine} - \text{SPT}_{Standing}) * \text{Ant}_{Co} \quad \text{(Eq. 4)}$$

$$\text{Inclination}_{Standing} = \text{Inclination}_{Supine} + (\text{SPT}_{Supine} - \text{SPT}_{Standing}) * \text{Inc}_{Co} \quad \text{(Eq. 5)}$$

Where $\text{Ant}_{Co}$ is an anteversion coefficient and $\text{Inc}_{Co}$ is an inclination coefficient. In some embodiments, the anteversion coefficient is 0.75. In some embodiments the anteversion coefficient is a value within the range of 0.7-0.8. In some embodiments it is a value within the range of 0.6-1. In some embodiments, the inclination coefficient is 0.29. In some embodiments, the inclination coefficient is a value within the range of 0.2-0.4.

Each time the user modifies the supine anteversion and inclination values, the system automatically inputs the values into Equations 2-5 to determine the standing and sitting anteversion and inclination values of the acetabular cup component. The embodiments in which the standing anteversion and inclination and/or the sittings anteversion and inclination values are adjustable includes the system automatically calculating the non-adjusted anteversion and inclination values in accordance with algebraically reorganized expressions of Equations 2-5.

In some embodiments, the system provides the user with view modification elements to allow the surgeon to manipulate the orientation of the pelvis and in turn the acetabular cup component. View modification elements include but are not limited to an AP view toggle, a lateral view toggle, and a slider style control that rotates the pelvis about its Z-axis. Alternative controls may be provider to enable a user to modify the view of the pelvis/acetabular cup component.

Intraoperative Analysis

Figure 21:
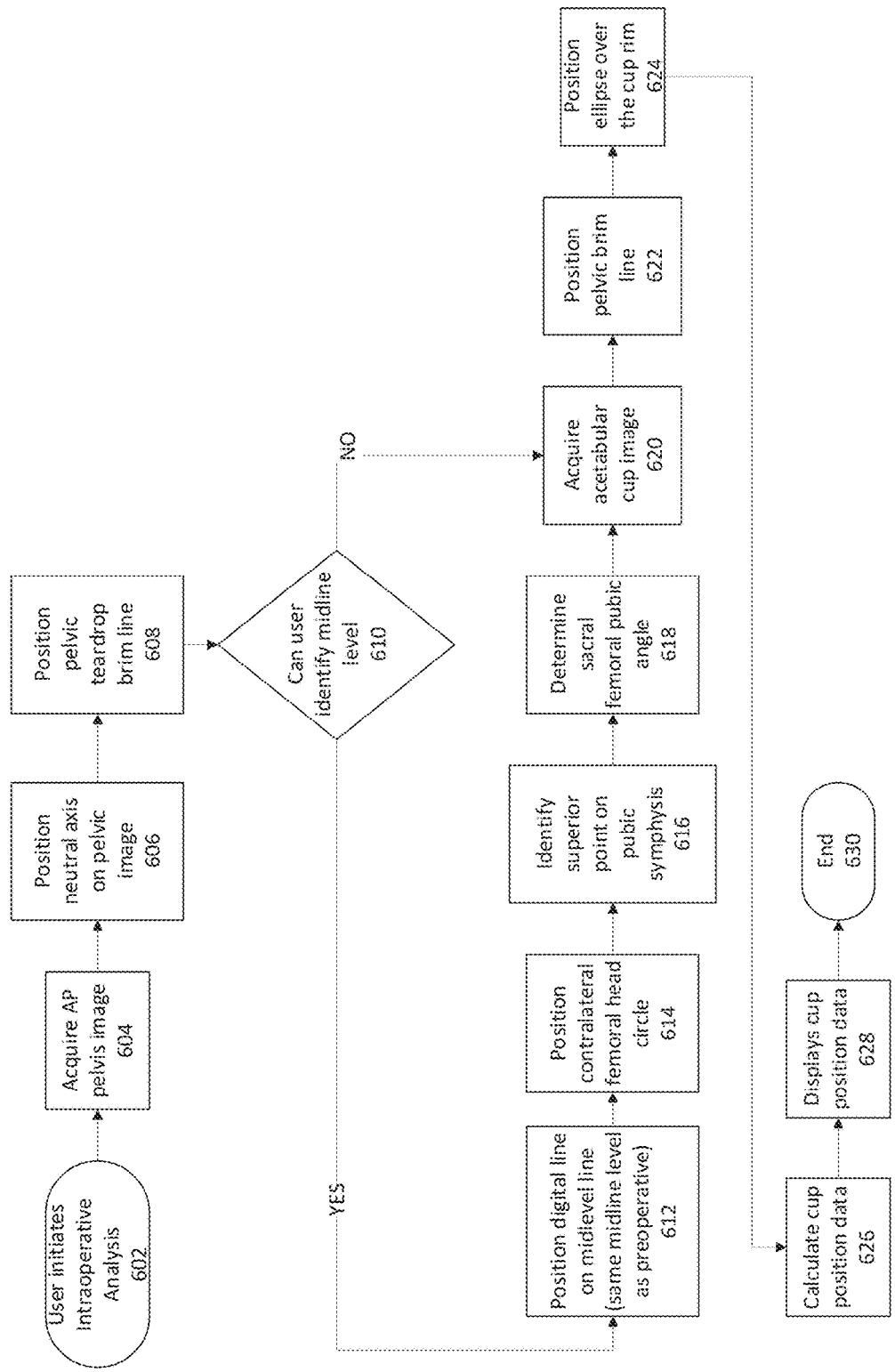
FIG. 21 is a flowchart capturing an embodiment of the steps of preoperative analysis.

Some embodiments include an intraoperative analysis performed by intraoperative module 300. The intraoperative analysis relies on the pelvic position data to calculate inclination and anteversion data during surgery. To do this, an embodiment of the intraoperative module 300 performs the steps detailed in the flowchart in FIG. 21.

The intraoperative analysis is initiated at step 602 either automatically or in response to a user instructing intraoperative module 300 to execute the intraoperative analysis. At step 604, image acquisition module 302 acquires an intraoperative AP image of a patient's pelvic region while the patient is in a supine position on an OR table. In most cases, intraoperative images will be taken using a fluoroscopic c-arm. However, the intraoperative images may be retrieved in any manner known to a person of ordinary skill in the art. In addition, the image may be loaded into the system through a direct cable connection or any other communication method.

Some embodiments include an image orientation step to modify one or more images to better capture the patient's pelvic position/orientation as it exists in the OR. Alternatively, the image capturing device is first properly oriented prior to capturing the image to ensure that the image depicts the pelvis in the same position/orientation as it exists in reality. In some embodiments, the user is provided with the option to manually rotate the intraoperative image as needed to better capture the true orientation of a patient's pelvis in reality. In some embodiments, the system will use pelvic position change data as input into the acetabular component positioning intraoperative module to account for pelvic position and/or c-arm position changes when calculating anteversion and inclination.

Figure 22:
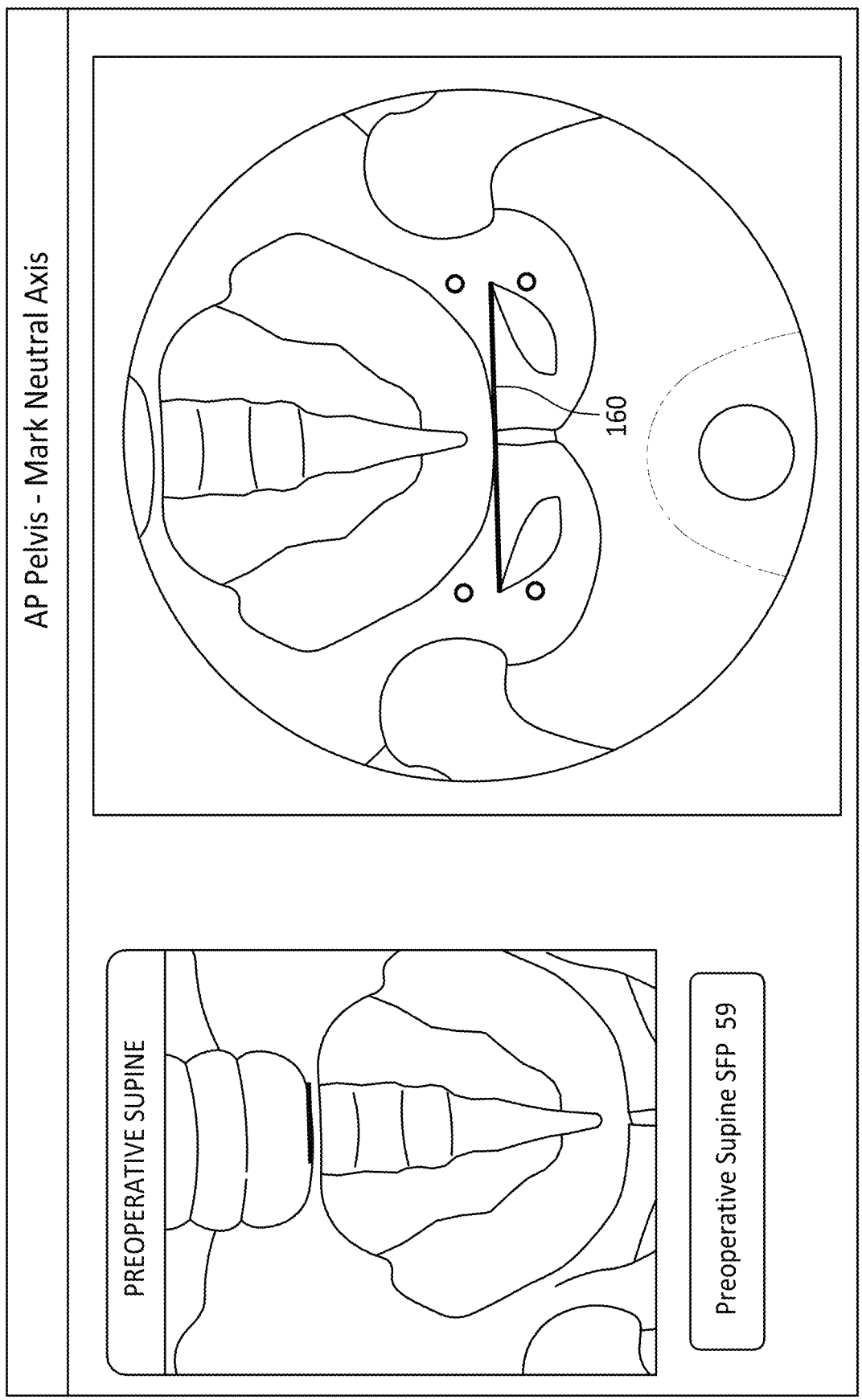
FIG. 22 is an exemplary intraoperative supine anteroposterior image of a patient's pelvic region depicting the step in which a neutral axis is drawn across the pelvis.

Once the intraoperative AP image is acquired, image annotation module 304 then digitally registers an anatomical landmark in the form of line 160 across the neutral axis at step 606 (see FIG. 22). The neutral axis (aka the "transteardrop axis") is a line extending between the inferior points on both pelvic teardrops. In some embodiments, the neutral axis is a line extending to consistent points on the ischial tuberosity structures.

Similar to the preoperative analysis, the anatomical landmark used in the intraoperative analysis may be points, lines, circles, or other types of digitally registerable annotations corresponding to one or more aspects of the patient's anatomy. In some embodiments, the anatomical landmarks are determined manually by a user. In some embodiments, image annotation module 304 automatically identifies the anatomical landmarks through image recognition software or machine learning algorithms. Some embodiments employ a mix of automated and manual identification of the anatomical landmarks. Moreover, some embodiments, allow the user to modify the location of the visually displayed anatomical landmarks points to account for imaging or location errors.

In some embodiments, some or all of the anatomical landmarks are digitally inserted or overlaid onto the images to provide a visual indication of the location of the anatomical landmarks. While different methods of visually displaying the landmarks may be used, the term "digitally register" will be used herein to refer to any method used to visually depict an anatomical landmark on a digital image. In some embodiments, intraoperative module 300 visually displays to a user each instance in which an anatomical landmark is digitally registered on one of the intraoperative images similar to FIGS. 22-28.

Figure 23:
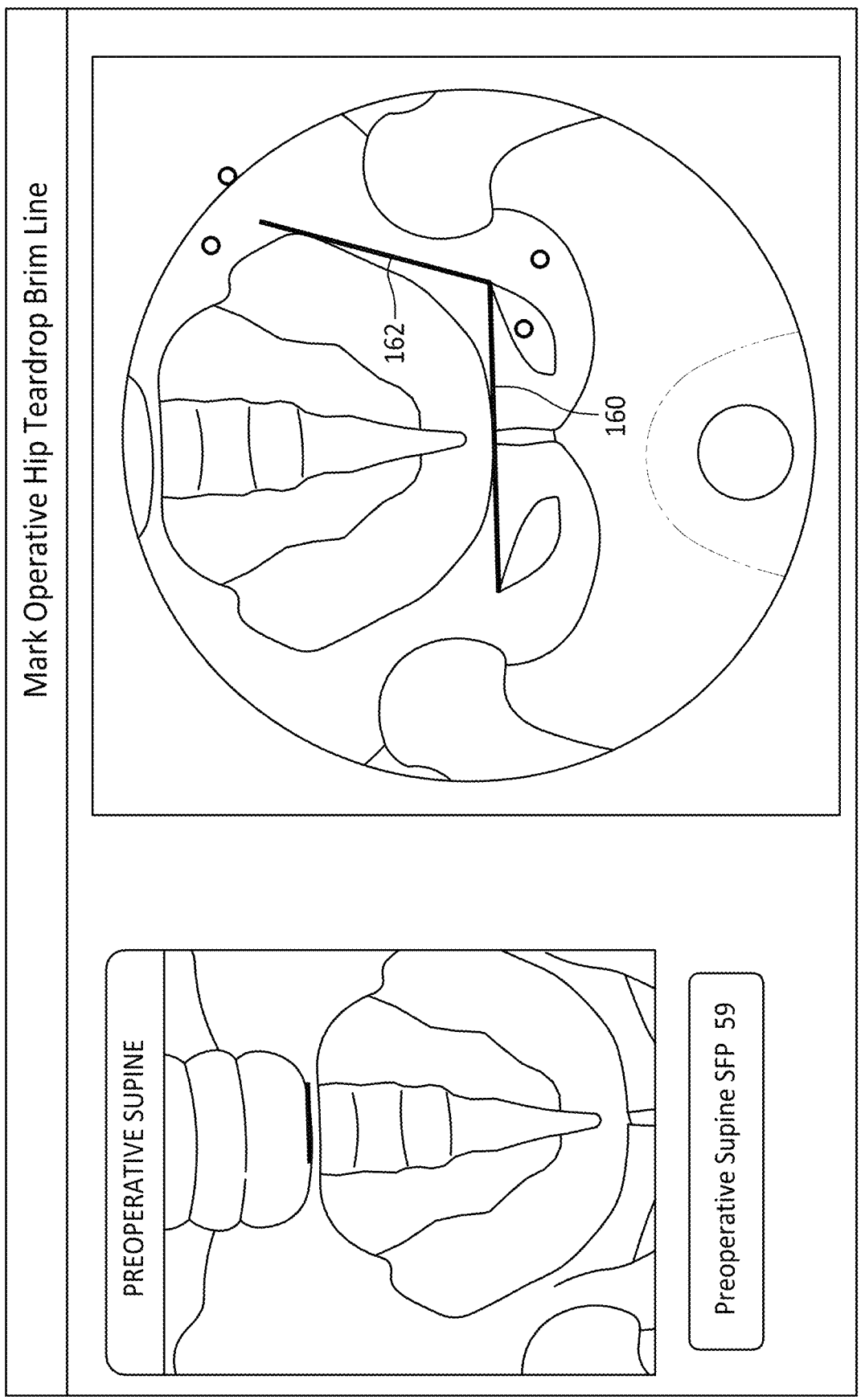
FIG. 23 is an exemplary intraoperative supine anteroposterior image of a patient's pelvic region depicting the step in which a teardrop brim line is drawn across the pelvis.

Referring back to FIG. 21, at step 608, the user or system identifies the operative hip and annotation module 304 digitally registers pelvic teardrop brim line 162, which is illustrated in FIG. 23. Pelvic teardrop brim line 162 extends between the pelvic teardrop on the operative hip and runs across the pelvic brim. Because teardrop brim line 162 runs tangential to the pelvic brim there is no need for a specific end point for the superior end of the line.

At step 610, the user and/or the system determines if the same vertebral anatomical landmark (the S1 endplate in the examples above) that was used to calculate the SFP angle in the preoperative images is visible/identifiable in the AP intraoperative image of the pelvis. Depending on the fluoroscopic c-arm used, it is possible that the vertebral anatomical landmark will not be clearly identifiable in the intraoperative pelvis image. If this happens, the system can skip steps 612-618, and instead use the SFP angle from the preoperative AP supine image and move to step 620. The preoperative SFP angle should be a close approximation to the intraoperative SFP angle. For best accuracy, the surgeon should review the obturator foramen openings and confirm that they are consistent between the preoperative and intraoperative images. This will ensure that the SFP angle in the preoperative and intraoperative AP supine images are generally consistent.

Figure 24:
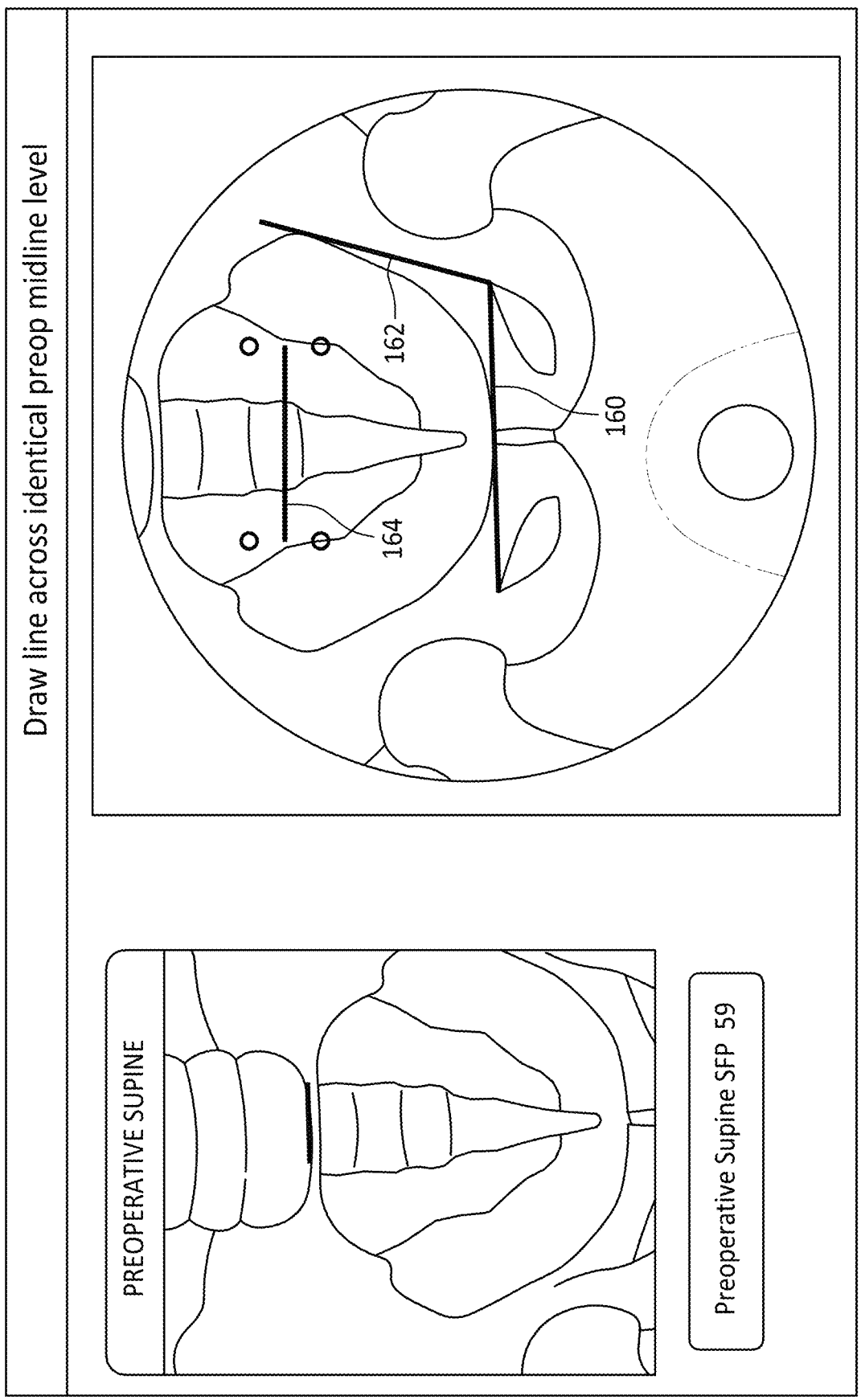
FIG. 24 is an exemplary intraoperative supine anteroposterior image of a patient's pelvic region depicting the step in which a line is drawn across the S1 upper endplate.
Figure 25:
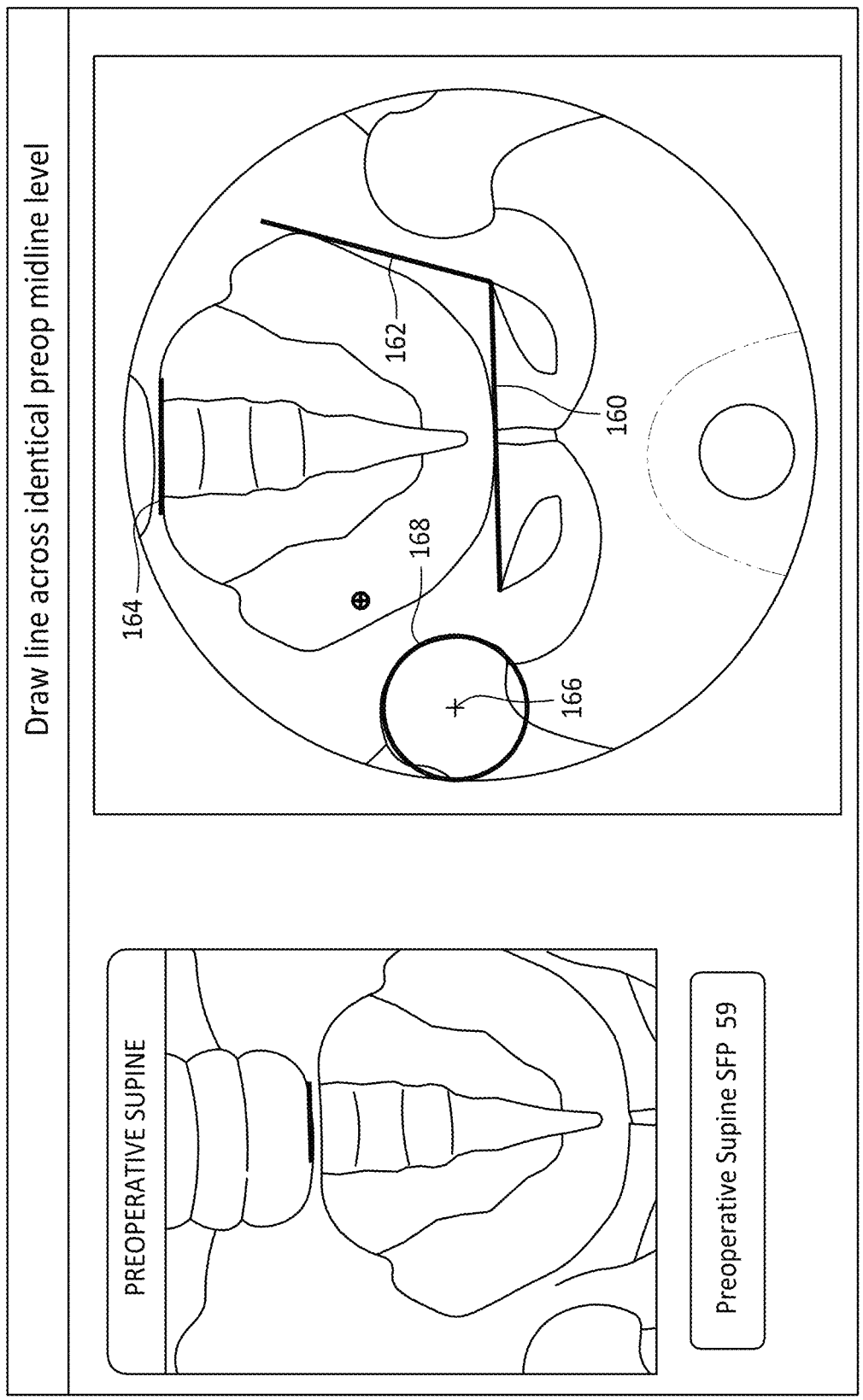
FIG. 25 is an exemplary intraoperative supine anteroposterior image of a patient's pelvic region depicting the step in which a circle is drawn around the contralateral femoral head.
Figure 26:
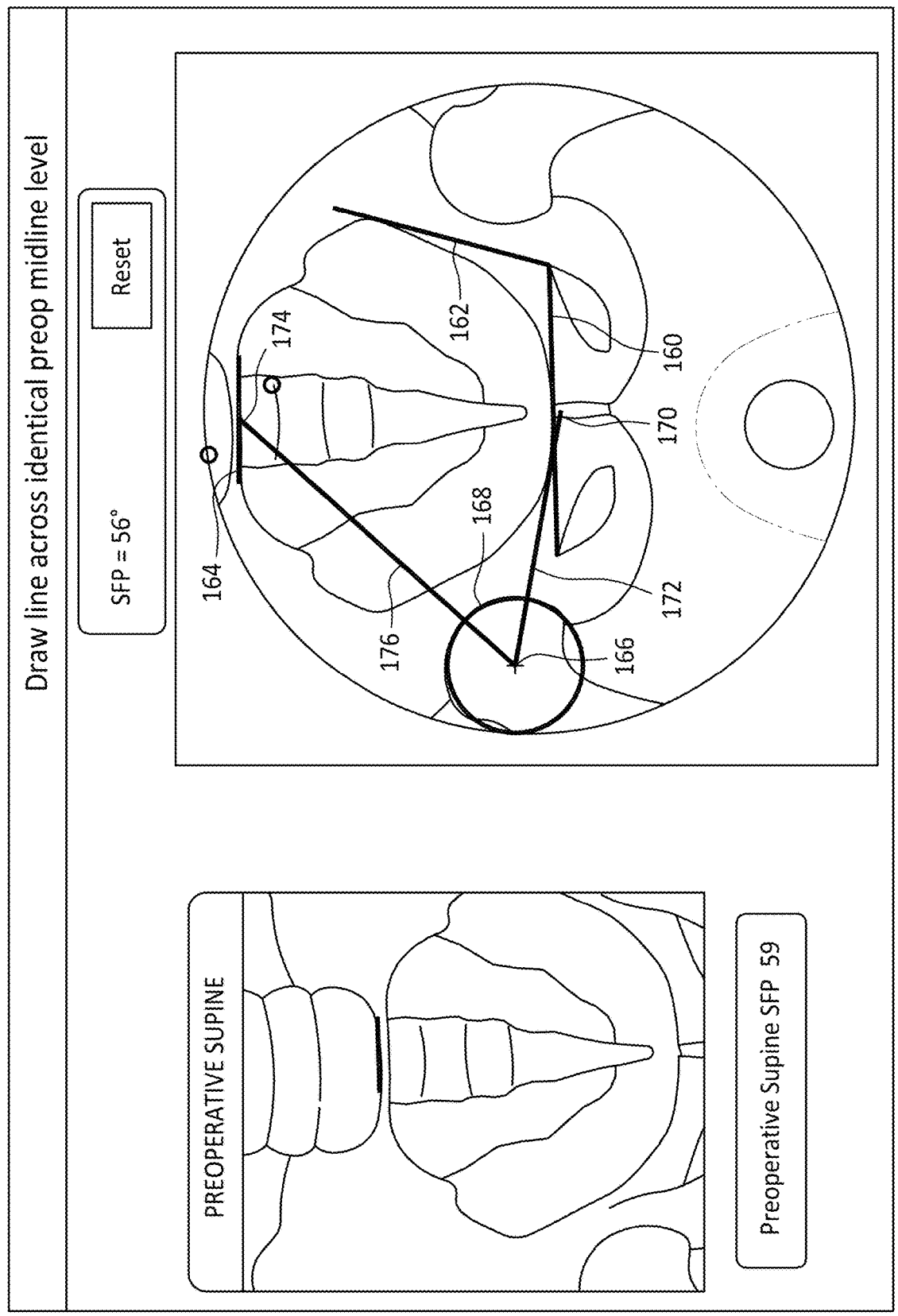
FIG. 26 is an exemplary intraoperative supine anteroposterior image of a patient's pelvic region depicting the step in which the SFP angle is calculated and displayed.

If the vertebral anatomical landmark is clearly identifiable in the intraoperative pelvis image, at step 612, image annotation module 304 positions digital line 164 across the vertebral anatomical landmark consistent with what was used in the preoperative analysis (see FIG. 24). Then at step 614, image annotation module 304 identifies center point 166 of the contralateral femoral head using digitally registered circle 168 as shown in FIG. 25. At step 616, image annotation module 304 digitally registers superior point 170 on the pubic symphysis. Calculation engine 306 can then determine the SFP angle based on first line 176 extending between center 166 of the contralateral femoral head and midpoint 174 of the vertebral anatomical landmark line and second line 172 extending between center 166 of the contralateral femoral head and superior point 170 on pubic symphysis. The angle between the two lines is the SFP angle. Calculation engine 306 determines the SFP angle at step 618 and pelvic position display module 308 displays the angle as shown in FIG. 26.

In some embodiments, if the SFP angle in the intraoperative image varies by more than 5 degrees of the SFP angle calculated in the preoperative supine image, a warning message will be displayed. This is a prompt to verify that the same vertebral anatomical landmark was used in calculating the SFP angle. If there is less than a 5-degree difference, the intraoperative module moves to step 620.

If the vertebral anatomical landmark is not clearly identifiable in the intraoperative pelvis image, the system provides an option to alternatively use the SFP angle calculated in the preoperative supine image and move on to step 620. The preoperative SFP angle should be a close approximation to the intraoperative SFP angle shown in the supine intraoperative image. The surgeon should visually confirm that the pelvis appears consistent by visual examination of the obturator foramen openings in the preoperative and intraoperative radiographic images.

At step 620, image acquisition module 302 acquires an intraoperative image of the implanted acetabular cup component. In most cases, intraoperative images will be taken using a fluoroscopic c-arm. However, the intraoperative images may be retrieved in any manner known to a person of ordinary skill in the art. In addition, the image may be loaded into the system through a direct cable connection or any other communication method.

Figure 27:
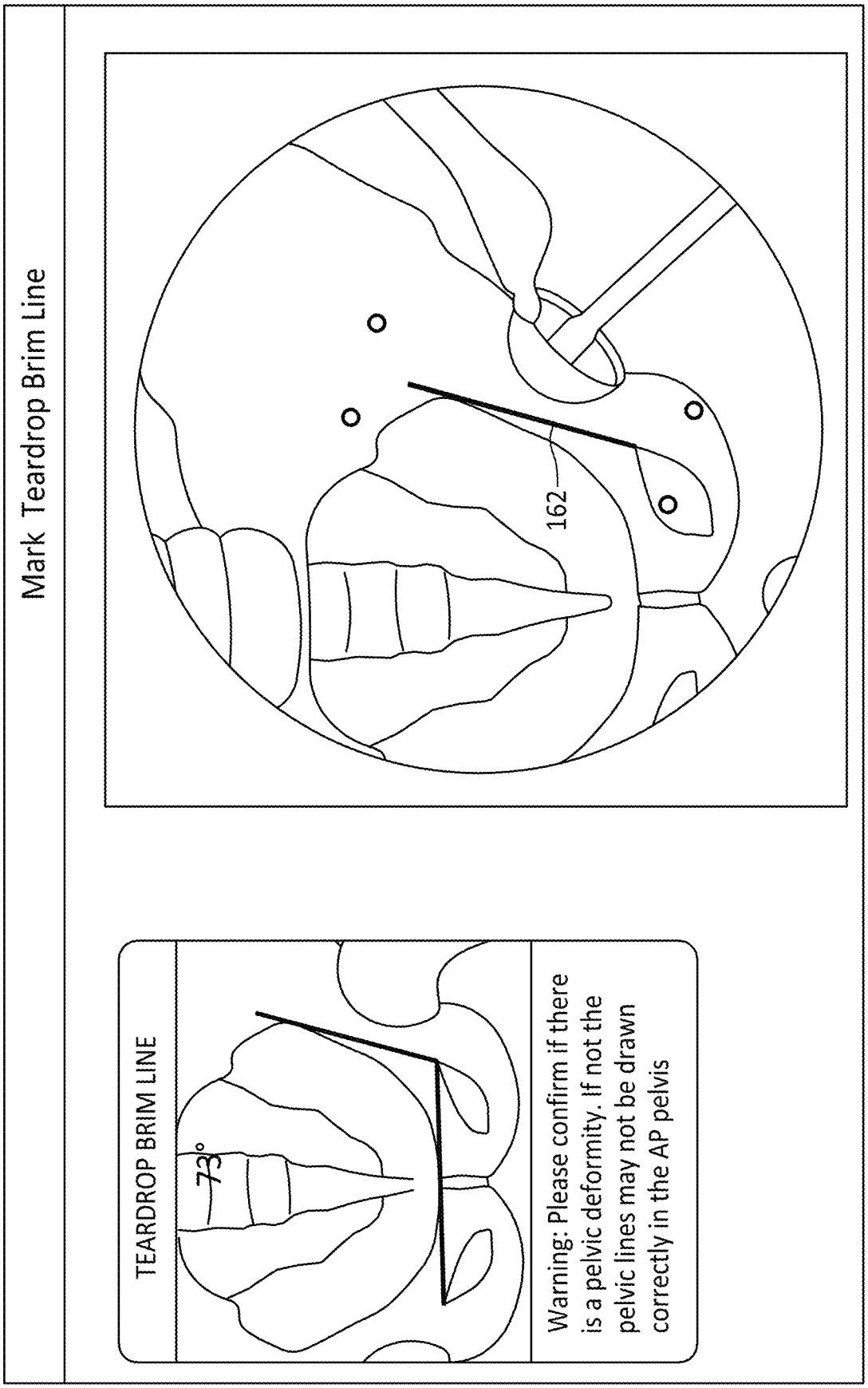
FIG. 27 is an exemplary intraoperative supine anteroposterior image of a patient's pelvic region depicting the step in which the intraoperative image of the acetabular cup component is displayed.

At step 622, image annotation module 304 digitally registers teardrop brim line 162 on the intraoperative image of the implanted acetabular cup component, which is illustrated in FIG. 27. Teardrop brim line 162 runs tangential to the pelvic brim so there is no need for a specific end point for the superior end of the line. The software uses this line to correlate the neutral axis on the intraoperative image of the pelvis to the image of the implanted acetabular cup component. Note that the use of two images—with the acetabulum centered on the screen in one—is used to minimize any parallax effect.

Figure 28:
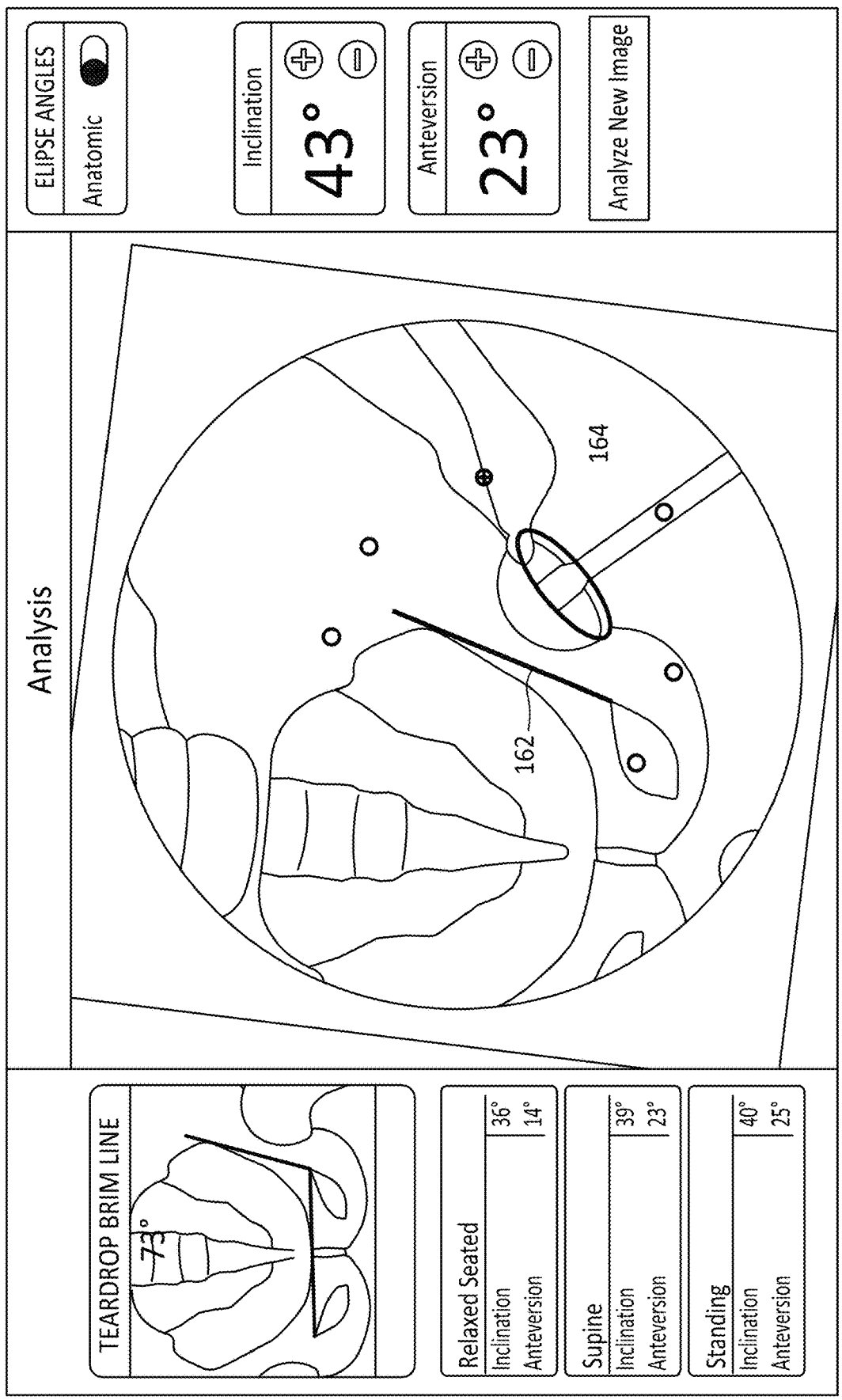
FIG. 28 is an embodiment of a graphic display of the hip dislocation risk in a standing, seated, and lying orientation based on the intraoperative analysis.

At step, 624 the user manually, or image annotation module 304 automatically, digitally registers tracking ellipse 164 over the rim of the acetabular cup component as shown in FIG. 28. The intraoperative placement of digital tracking ellipse 164 assists in calculating anteversion and inclination in the operative position as well as in the seated and standing positions based upon changes in pelvic tilt.

The ellipse is drawn so that the major axis of the ellipse represents the inclination angle relative to the neutral axis. Thus, increasing/decreasing anteversion will appropriately increase/decrease the size of the digital tracking ellipse's minor axis, consistent with the calculation. Similarly, a user can increase/decrease the inclination of the ellipse, which will appropriately increase/decrease the angle of the digital tracking ellipse's major axis, relative to the neutral axis and associated to the neutral axis in the image of the pelvis through the identification of the pelvic brim line in each image.

In other words, adjusting the inclination will rotate the ellipse and adjusting the anteversion will expand or contract the ellipse opening. In some embodiments, ellipse angle data can be displayed using either the anatomic or radiographic mode. The anatomic mode is recommended because it corrects for 3-d to 2-d image differences and for this reason it provides a more accurate depiction of anteversion and inclination. In some embodiments, the system displays the image of the pelvis in a small "picture in picture" window and depicts both the "pelvic brim" and "neutral axis" or "trans-teardrop" lines.

In some embodiments, the user can manually position the ellipse, using a digital handle, so that it overlays the opening of the acetabular component in the radiographic image being analyzed. The user may resize and reposition the ellipse as required. In some embodiments, the surgeon can continue to re-position the acetabular cup component, and shoot additional images, until the ellipse and image indicate that they have matched their desired inclination and anteversion.

The image of (1) the pelvis and (2) the centered acetabular component will be rotated on screen so that the neutral axes are aligned along the x-axis of the screen. This will ensure that the inclination represented by the digital tracking ellipse will always appear consistently on the screen, which is beneficial for users.

Once the tracking ellipse positioning is complete, the system can use the location of the tracking ellipse to determine the intraoperative anatomic inclination and anteversion of the acetabulum cup component shown in the intraoperative image. It should be noted that other systems and methods known to a person of ordinary skill in the art for tracking the position and orientation of implanted objects can be used to determine the position and orientation of the acetabular cup component shown in the intraoperative image(s).

At step 626, calculation engine 306 uses preoperative pelvic positioning ("pelvic tilt") data from output communication module 210 and intraoperative data to calculate anteversion and inclination data of the acetabular cup component for the relaxed seated, supine and standing positions. These calculations incorporate the patient's unique SFP information to calculate the effect of pelvic position data from the preoperative analysis that was previously performed.

More specifically, the system can determine the anteversion and inclination of the acetabular cup component in the seated, supine, and standing anatomical positions through Equations 6-12 below. Equation 6 establishes the intraoperative sacral slope based on the pelvic incidence, SFP constant, and measured intraoperative SFP angle.

$$SS_I = PI - (SFP_{constant} - SFP_I) \quad (Eq.\ 6)$$

where $SS_I$ is the intraoperative sacral slope, PI is the pelvic incidence (which remains constant for a patient in any anatomical position), $SFP_{constant}$ is the constant that provides the relationship between SFP and SPT angles as introduced in Eq. 1, and $SFP_I$ is the measured SFP angle in the intraoperative image. If the SFP angle in the intraoperative supine image cannot be accurately determined, the $SFP_I$ in Eq. 6 is replaced with the preoperative SFP angle.

Equations 7-12 are then used to calculate the inclination and anteversion values when the patient is in the seated, supine, and standing anatomical positions.

$$Inclination_{Seated} = Inclination_m + (SS_{PSeated} - SS_I) * Inc_{Co} \quad (Eq.\ 7)$$

$$Anteversion_{Seated} = Anteversion_m + (SS_{PSeated} - SS_I) * Ant_{Co} \quad (Eq.\ 8)$$

$$Inclination_{Supine} = Inclination_m + (SS_{PSupine} - SS_I) * Inc_{Co} \quad (Eq.\ 9)$$

$$Anteversion_{Supine} = Anteversion_m + (SS_{PSupine} - SS_I) * Ant_{Co} \quad (Eq.\ 10)$$

$$Inclination_{Standing} = Inclination_m + (SS_{PStanding} - SS_I) * Inc_{Co} \quad (Eq.\ 11)$$

$$Anteversion_{Standing} = Anteversion_m + (SS_{PStanding} - SS_I) * Ant_{Co} \quad (Eq.\ 12)$$

Where $Ant_{Co}$ is an anteversion coefficient, $Inc_{Co}$ is an inclination coefficient, $Inclination_m$ is the measured inclination of the acetabular cup component in the intraoperative image, $Anteversion_m$ is the measured anteversion of the acetabular cup component in the intraoperative image, $SS_I$ is the intraoperative sacral slope, and $SS_{PSeated}$ is the preoperative sacral slope in the seated position, $SS_{PSupine}$ is the preoperative sacral slope in the supine position, and $SS_{PStanding}$ is the preoperative sacral slope in the standing position.

In some embodiments, the anteversion coefficient is 0.75. In some embodiments the anteversion coefficient is a value within the range of 0.7-0.8. In some embodiments it is a value within the range of 0.6-1. In some embodiments, the inclination coefficient is 0.29. In some embodiments, the inclination coefficient is a value within the range of 0.2-0.4.

At step 628, acetabular component display module 308 displays the images to the user and acetabular component position output module 310 presents the position data to the user on a graphic interface similar to FIG. 28. Based on the patient's intraoperative pelvic tilt and the inclination and anteversion angles of the implanted cup component, the system displays the dislocation risk of the prosthetic hip when the patient is seated, standing, and lying as depicted in an exemplary form on the left side of the screen. Moreover, the inclination values and anteversion values are displayed and the end user is provided with the ability to adjust the anteversion and inclination values of the acetabular cup component using the graphic interface buttons. The inclination and anteversion can be adjusted in both the positive and negative directions. When the end user modifies the inclination and anteversion of the acetabular cup, the system recalculates the dislocation risk in each position to determine if the acetabular cup component needs to be readjusted.

Preferably the display includes both a quantitative measurement of the anteversion and inclination values for the various anatomic locations and qualitative indicators (colors to identify a safe zone, a medium dislocation risk zone, and a high dislocation risk zone) to convey the risk of dislocation when the patient is in various anatomical positions. If the values are green, the patient is in a safe zone. If the values are yellow, the patient is in a medium risk zone. And if the values are red, the patient is in a high-risk zone. Similar to FIGS. 20, the display may include a tilt bar that includes both a quantitative measurement and a qualitative assessment of the risk of dislocation when the patient is sitting, lying, and standing.

Hardware and Software Infrastructure Examples

The present invention may be embodied on various computing systems and/or platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method comprising:
    acquiring a first anteroposterior image of a patient's pelvic region when the patient is in a first anatomical position, a lateral image of the patient's pelvic region when the patient is in the first anatomical position, and a second anteroposterior image of the patient's pelvic region when the patient is in a second anatomical position different from the first anatomical position;
    determining a first reference angle from the first anteroposterior image of the patient's pelvic region in the first anatomical position, wherein the first reference angle is measured between (i) a line connecting a femoral reference point in the first anteroposterior image to a pubic reference point in the first anteroposterior image and (ii) a line connecting the femoral reference point in the first anteroposterior image to a sacral reference point in the first anteroposterior image;
    determining a first pelvic tilt angle from the lateral image of the patient's pelvic region in the first anatomical position;
    determining a patient-specific constant by summing the first reference angle and the first pelvic tilt angle;
    determining a second reference angle from the second anteroposterior image of the patient's pelvic region in the second anatomical position, wherein the second reference angle is measured between (i) a line connecting the femoral reference point in the second anteroposterior image to the pubic reference point in the second anteroposterior image and (ii) a line connecting the femoral reference point in the second anteroposterior image to the sacral reference point in the second anteroposterior image; and
    determining a second pelvic tilt angle corresponding to the second anatomical position by subtracting the second reference angle from the patient-specific constant.

2. The method of claim 1, wherein the first anatomical position is a standing position, and wherein the second anatomical position is a supine position.

3. The method of claim 2, wherein:
    the first anteroposterior image and the lateral image are preoperative images;
    the second anteroposterior image is an intraoperative image and depicts an acetabular cup component positioned in the patient's pelvic region; and
    the method further comprises:
        determining an intraoperative supine inclination and an intraoperative supine anteversion of the acetabular cup component from the second anteroposterior image; and calculating an expected standing inclination of the acetabular cup component and an expected standing anteversion of the acetabular cup component when the patient is in the standing position based on the intraoperative supine inclination of the acetabular cup component, the intraoperative supine anteversion of the acetabular cup component, the first pelvic tilt angle, and the second pelvic tilt angle.

4. The method of claim 1, wherein determining the first reference angle from the first anteroposterior image of the patient's pelvic region includes:
digitally registering a vertebral anatomical landmark as the sacral reference point in the first anteroposterior image;
digitally registering a center point of a femoral head as the femoral reference point in the first anteroposterior image; and
digitally registering a superior point on a pubic symphysis as the pubic reference point in the first anteroposterior image.

5. The method of claim 4, wherein determining the second reference angle from the second anteroposterior image of the patient's pelvic region includes:
digitally registering the vertebral anatomical landmark as the sacral reference point in the second anteroposterior image;
digitally registering the center point of the femoral head as the femoral reference point in the second anteroposterior image; and
digitally registering the superior point on the pubic symphysis as the pubic reference point in the second anteroposterior image.

6. The method of claim 1, wherein determining the first pelvic tilt angle from the lateral image includes directly determining the first pelvic tilt angle by:
digitally registering a vertebral anatomical landmark on the lateral image, wherein the vertebral anatomical landmark is a midpoint on a line corresponding to the patient's sacral endplate;
digitally registering a center point of a femoral head on the lateral image;
digitally registering a vertical axis on the lateral image that intersects the center point of the femoral head; and
calculating the first pelvic tilt angle as the angle between the vertical axis and a line connecting the center point of the femoral head to the vertebral anatomical landmark.

7. The method of claim 1, wherein determining the first pelvic tilt angle from the lateral image includes indirectly determining the first pelvic tilt angle by:
digitally registering a vertebral anatomical landmark on the lateral image, wherein the vertebral anatomical landmark is a line corresponding to the patient's sacral endplate;
digitally registering a horizontal axis on the lateral image that intersects a superior point on the line corresponding to the patient's sacral endplate;
determining a sacral slope angle, which corresponds to an angle between the horizontal axis and the vertebral anatomical landmark; and
calculating the first pelvic tilt angle by subtracting the sacral slope angle from a pelvic incidence of the patient.

8. The method of claim 1, wherein determining the first reference angle from the first anteroposterior image of the patient's pelvic region and determining the second reference angle from the second anteroposterior image of the patient's pelvic region each comprise:
positioning a circle around a femoral head in the respective anteroposterior image to digitally register the femoral reference point;
positioning a marker on a superior point of the pubic symphysis in the respective anteroposterior image to digitally register the pubic reference point; and
positioning a line between two features of the patient's sacrum in the respective anteroposterior image to digitally register the sacral reference point as the midpoint of the positioned line.

9. The method of claim 8, wherein positioning the line between two features of the patient's sacrum comprises positioning the line between anterior and lateral aspects of the patient's S1 joint.

10. The method of claim 1, wherein:
the first anteroposterior image, the lateral image, and the second anteroposterior image are preoperative images; and
the method further comprises:
determining a planned inclination and a planned anteversion for an acetabular cup component to be implanted in the patient's pelvic region, wherein the planned inclination and the planned anteversion correspond to the second anatomical position of the patient; and
calculating an expected inclination and an expected anteversion for the acetabular cup component when the patient is in the first anatomical position based on the planned inclination corresponding to the second anatomical position, the planned anteversion corresponding to the second anatomical position, the first pelvic tilt angle, and the second pelvic tilt angle.

11. A method comprising:
acquiring a first anteroposterior image of a patient's pelvic region when the patient is in a first anatomical position, a lateral image of the patient's pelvic region when the patient is in the first anatomical position, and a second anteroposterior image of the patient's pelvic region when the patient is in a second anatomical position different from the first anatomical position;
determining a first reference angle from the first anteroposterior image, wherein the first reference angle is measured between (i) a line connecting a femoral reference point in the first anteroposterior image to a pubic reference point in the first anteroposterior image and (ii) a line connecting the femoral reference point in the first anteroposterior image to a sacral reference point in the first anteroposterior image;
determining a first pelvic tilt angle from the lateral image;
determining a second reference angle from the second anteroposterior image, wherein the second reference angle is measured between (i) a line connecting the femoral reference point in the second anteroposterior image to the pubic reference point in the second anteroposterior image and (ii) a line connecting the femoral reference point in the second anteroposterior image to the sacral reference point in the second anteroposterior image; and
determining a second pelvic tilt angle corresponding to the second anatomical position by subtracting the second reference angle from the sum of the first reference angle and the first pelvic tilt angle.

12. The method of claim 11, wherein determining the first reference angle from the first anteroposterior image of the patient's pelvic region and determining the second reference angle from the second anteroposterior image of the patient's pelvic region each comprise:

positioning a circle around a femoral head in the respective anteroposterior image to digitally register the femoral reference point;

positioning a marker on a superior point of the pubic symphysis in the respective anteroposterior image to digitally register the pubic reference point; and positioning a line between two features of the patient's sacrum in the respective anteroposterior image to digitally register the sacral reference point as the midpoint of the positioned line.

13. The method of claim 12, wherein positioning the line between two features of the patient's sacrum comprises positioning the line between anterior and lateral aspects of the patient's S1 joint.

14. The method of claim 11, wherein the first pelvic tilt angle is measured between (i) a vertical line intersecting the femoral reference point in the lateral image and (ii) a line connecting the femoral reference point in the lateral image to the sacral reference point in the lateral image.

15. The method of claim 14, wherein determining the first pelvic tilt angle from the lateral image of the patient's pelvic region comprises:

positioning a circle around a femoral head in the lateral image to digitally register the femoral reference point; and positioning a line along the patient's S1 joint, wherein the midpoint of the positioned line defines the sacral reference point in the lateral image.

16. The method of claim 11, wherein the first anatomical position is a standing position, and wherein the second anatomical position is a supine position.

17. The method of claim 16, wherein:

the first anteroposterior image, the lateral image, and the second anteroposterior image are preoperative images; and the method further comprises:

determining a planned inclination and a planned anteversion for an acetabular cup component to be implanted in the patient's pelvic region, wherein the planned inclination and the planned anteversion correspond to the supine position of the patient; and calculating an expected inclination and an expected anteversion for the acetabular cup component when the patient is in the standing position based on the planned inclination corresponding to the supine position, the planned anteversion corresponding to the supine position, the first pelvic tilt angle, and the second pelvic tilt angle.

18. The method of claim 17, further comprising:

acquiring a preoperative lateral image of the patient's pelvic region when the patient is in a seated position;

determining a third pelvic tilt angle from the preoperative lateral image of the patient's pelvic region when the patient is in a seated position; and calculating an expected inclination and an expected anteversion for the acetabular cup component when the patient is in the seated position based on the planned inclination corresponding to the supine position, the planned anteversion corresponding to the supine position, the third pelvic tilt angle, and the second pelvic tilt angle.

19. The method of claim 16, wherein:

the first anteroposterior image and the lateral image are preoperative images;

the second anteroposterior image is an intraoperative image and depicts an acetabular cup component positioned in the patient's pelvic region; and the method further comprises:

determining an intraoperative supine inclination and an intraoperative supine anteversion of the acetabular cup component from the second anteroposterior image; and calculating an expected standing inclination for the acetabular cup component and an expected standing anteversion for the acetabular cup component when the patient is in the standing position based on the intraoperative supine inclination of the acetabular cup component, the intraoperative supine anteversion of the acetabular cup component, the first pelvic tilt angle, and the second pelvic tilt angle.

20. The method of claim 19, further comprising:

acquiring a preoperative lateral image of the patient's pelvic region when the patient is in a seated position;

determining a third pelvic tilt angle from the preoperative lateral image of the patient's pelvic region when the patient is in a seated position; and calculating an expected seated inclination for the acetabular cup component and an expected seated anteversion for the acetabular cup component when the patient is in the seated position based on the intraoperative supine inclination of the acetabular cup component, the intraoperative supine anteversion of the acetabular cup component, the third pelvic tilt angle, and the second pelvic tilt angle.

\* \* \* \* \*